(12) United States Patent
Chen et al.

(10) Patent No.: US 11,365,424 B2
(45) Date of Patent: Jun. 21, 2022

(54) ABIOTIC STRESS TOLERANT PLANTS AND POLYNUCLEOTIDES TO IMPROVE ABIOTIC STRESS AND METHODS

(71) Applicants: SINOBIOWAY BIO-AGRICULTURE GROUP CO LTD., Beijing (CN); PIONEER OVERSEAS CORPORATION, Johnston, IA (US)

(72) Inventors: Guangwu Chen, Beijing (CN); Yang Gao, Beijing (CN); Guihua Lu, Beijing (CN); Guanfan Mao, Beijing (CN); Changgui Wang, Beijing (CN); Guokui Wang, Beijing (CN)

(73) Assignees: SINOBIOWAY BIO-AGRICULTURE GROUP CO LTD; PIONEER OVERSEAS CORPORATION

( * ) Notice: Subject to any disclaimer, the term of this patent is extended or adjusted under 35 U.S.C. 154(b) by 0 days.

(21) Appl. No.: 16/760,504

(22) PCT Filed: Nov. 1, 2018

(86) PCT No.: PCT/CN2018/113324
§ 371 (c)(1),
(2) Date: Apr. 30, 2020

(87) PCT Pub. No.: WO2019/085962
PCT Pub. Date: May 9, 2019

(65) Prior Publication Data
US 2020/0255852 A1    Aug. 13, 2020

(30) Foreign Application Priority Data
Nov. 2, 2017   (CN) .......................... 201711062544.0

(51) Int. Cl.
*C12N 15/82* (2006.01)
*C07K 14/415* (2006.01)
*C12N 9/22* (2006.01)

(52) U.S. Cl.
CPC ........ *C12N 15/8273* (2013.01); *C07K 14/415* (2013.01); *C12N 9/22* (2013.01); *C12N 2310/20* (2017.05)

(58) Field of Classification Search
None
See application file for complete search history.

(56) References Cited

U.S. PATENT DOCUMENTS

| 8,329,991 B2 | 12/2012 | Shirley et al. |
| 2006/0123505 A1* | 6/2006 | Kikuchi ............... C07K 14/415 800/278 |
| 2016/0319296 A1 | 11/2016 | Gao et al. |

FOREIGN PATENT DOCUMENTS

| JP | 2005185101 | 7/2005 |
| WO | 2008116829 | 2/2008 |

OTHER PUBLICATIONS

International Search Report and Written Opinion PCT/CN2018/113324, dated Jan. 30, 2019.
GenBank Accession: HV087493.1, GenBank Database Jul. 15, 2011.
GenBank Accession: XM_015762871, GenBank Database Mar. 1, 2016.

* cited by examiner

*Primary Examiner* — Elizabeth F McElwain

(57) ABSTRACT

Isolated polynucleotides and polypeptides, and recombinant DNA constructs are useful for conferring improved drought tolerance. Compositions (such as plants or seeds) comprising these recombinant DNA constructs; and methods utilizing these recombinant DNA constructs. The recombinant DNA constructs comprise a polynucleotide operably linked to a promoter that is functional in a plant, wherein said polynucleotides encode drought tolerance polypeptides.

12 Claims, No Drawings
Specification includes a Sequence Listing.

ABIOTIC STRESS TOLERANT PLANTS AND POLYNUCLEOTIDES TO IMPROVE ABIOTIC STRESS AND METHODS

FIELD

The field of the disclosure relates to plant breeding and genetics and, particularly, relates to recombinant DNA constructs useful in plants for improving tolerance to abiotic stress, such as drought and cold stress.

BACKGROUND

Stresses to plants may be caused by both biotic and abiotic agents. For example, biotic stresses include infection with pathogen, insect feeding, and parasitism by another plant such as mistletoe. Abiotic stresses include, for example, excessive or insufficient available water, temperature extremes, and synthetic chemicals such as herbicides.

Abiotic stress is the primary cause of crop loss worldwide, causing average yield losses more than 50% for major crops (Boyer, J. S. (1982) *Science* 218:443-448; Bray, E. A. et al. (2000) In Biochemistry and Molecular Biology of Plants, edited by Buchannan, B. B. et al., Amer. Soc. Plant Biol., pp. 1158-1249). Plants are sessile and have to adjust to the prevailing environmental conditions of their surroundings. This has led to their development of a great plasticity in gene regulation, morphogenesis, and metabolism. Adaption and defense strategies involve the activation of genes encoding proteins important in the acclimation or defense towards the different stresses.

Drought is one of the major abiotic stresses that limit crop productivity worldwide, and exposure of plants to a water-limiting environment during various developmental stages appear to activate various physiological and developmental changes. Genetic research has shown that drought tolerance is a quantitative trait, controlled by many genes. Molecular marker-assisted breeding has led to improved drought tolerance in crops, and transgenic approaches to engineer drought tolerance in crops have made progress (Vinocur B. and Altman A. (2005) *Curr. Opin. Biotechnol.* 16:123-132; Lawlor D W. (2013) *J. Exp. Bot.* 64:83-108). However, there is a need to develop new compositions and methods to improve drought tolerance in crops. This invention provides such compositions and methods.

SUMMARY

The following embodiments are among those encompassed by the disclosure:

In one embodiment, the present disclosure includes an isolated polynucleotide, comprising: (a) a polynucleotide with a nucleotide sequence of at least 85% identity to SEQ ID NO: 1, 4, 7, 10 or 13; (b) a polynucleotide with a nucleotide sequence of at least 85% identity to SEQ ID NO: 2, 5, 8, 11 or 14; (c) a polynucleotide encoding a polypeptide with an amino acid sequence of at least 90% identity to SEQ ID NO: 3, 6, 9, 12 or 15; or (d) the full complement of the nucleotide sequence of (a), (b) or (c), wherein increased expression of the polynucleotide in a plant enhances drought tolerance. In certain embodiments, the isolated polynucleotide comprises the nucleotide sequence of SEQ ID NO: 1, 2, 4, 5, 7, 8, 10, 11, 13 or 14; and the polypeptide comprises the amino acid sequence of SEQ ID NO: 3, 6, 9, 12 or 15.

In another embodiment, the present disclosure includes a recombinant DNA construct comprising the isolated polynucleotide, optionally, operably linked to at least one heterologous regulatory element, wherein the polynucleotide comprises (a) a polynucleotide with a nucleotide sequence of at least 85% identity to SEQ ID NO: 1, 2, 4, 5, 7, 8, 10, 11, 13 or 14; (b) a polynucleotide encoding a polypeptide with an amino acid sequence of at least 90% identity to SEQ ID NO: 3, 6, 9, 12 or 15; or (c) the full complement of the nucleotide sequence of (a) or (b).

In another embodiment, the present disclosure includes a modified plant or seed comprising an increased expression of at least one polynucleotide encoding a polypeptide with an amino acid sequence of at least 90% identity to SEQ ID NO: 3, 6, 9, 12 or 15.

In certain embodiments, the modified plant comprises in its genome a recombinant DNA construct comprising a polynucleotide operably linked to at least one heterologous regulatory element, wherein the polynucleotide comprises (a) a polynucleotide with a nucleotide sequence of at least 85% identity to SEQ ID NO: 1, 2, 4, 5, 7, 8, 10, 11, 13 or 14; (b) a polynucleotide encoding a polypeptide with an amino acid sequence of at least 90% identity to SEQ ID NO: 3, 6, 9, 12 or 15; or (c) the full complement of the nucleotide sequence of (a) or (b).

In certain embodiments, the modified plant comprises a targeted genetic modification at a genomic locus that encodes a polypeptide with an amino acid sequence of at least 90% identity to SEQ ID NO: 3, 6, 9, 12 or 15; wherein the targeted genetic modification increases the level and/or activity of the encoded polypeptide.

In certain embodiments, the modified plant exhibits improved drought tolerance (e.g., increased survival rate, reduced leaf rolling degree, improved seed setting rate, and/or increased grain yield) compared to a control plant. In certain embodiments, the modified plant exhibits improved grain yield when grown under no abiotic stress conditions.

In another embodiment, methods are provided for increasing drought tolerance in a plant, the method comprises increasing the expression of at least one polynucleotide encoding a polypeptide with an amino acid sequence of at least 90% identity to SEQ ID NO: 3, 6, 9, 12 or 15. Wherein the obtained plant exhibits increased drought tolerance when compared to the control plant, and the said improved drought tolerance may be increased survival rate, reduced leaf rolling degree, improved seed setting rate, or increased grain yield under drought condition.

In certain embodiments, the expression of the polynucleotide is increased by a step selected from the group consisting of: (a) increasing the expression of the polynucleotide by introducing a recombinant DNA construct into the plant, wherein the recombinant DNA construct comprises a polynucleotide encoding a polypeptide having an amino acid sequence of at least 90% identity compared to SEQ ID NOs: 3, 6, 9, 12 or 15 operably linked to at least one heterologous regulatory element; or (b) increasing the expression of an endogenous polynucleotide encoding the polypeptide having an amino acid sequence of at least 90% identity compared to SEQ ID NO: 3, 6, 9, 12 or 15.

In another embodiment, methods are provided for enhancing grain yield in a rice plant, when compared to a control plant, wherein the plant exhibits enhanced grain yield under normal and/or stress conditions, the method comprising increasing the expression of at least one polynucleotide encoding a polypeptide with an amino acid sequence of at least 90% identity to SEQ ID NOs: 3, 6, 9, 12 or 15 in the plant.

In another embodiment, methods are provided for making a plant in which the expression or the activity of a polypeptide having an amino acid sequence of at least 90% identity compared to SEQ ID NOs: 3, 6, 9, 12 or 15 is increased, when compared to the expression or activity of the corresponding polypeptide from a control plant, wherein the plant exhibits at least one phenotype selected from the group consisting of: increased drought tolerance, increased grain yield, increased abiotic stress tolerance and increased biomass, compared to the control plant, wherein the method comprises the steps of (i) introducing a DNA fragment or deleting a DNA fragment or (ii) introducing one or more nucleotide changes in the genomic region comprising the endogenous gene encoding the polypeptide and its regulatory element, wherein the change is effective for increasing the expression or the activity of the endogenous polypeptide. In certain embodiments, the change is introduced using zinc finger nuclease, Transcription Activator-Like Effector Nuclease (TALEN), CRISPR-cas, guided Cas endonuclease, meganuclease or CRISPR-Cas ribonucleoprotein complexes.

In certain embodiments, the plant for use in the compositions and methods is selected from the group consisting of rice, maize, soybean, sunflower, sorghum, canola, wheat, alfalfa, cotton, barley, millet, sugar cane and switchgrass.

In another embodiment, methods are provided for identifying one or more alleles associated with drought tolerance in a population of rice plants, the method comprising: (a) detecting in a population of rice plants one or more polymorphisms in (i) a genomic region encoding a polypeptide or (ii) a regulatory region controlling expression of the polypeptide, wherein the polypeptide comprises the amino acid sequence selected from the group consisting of SEQ ID NO: 3, 6, 9, 12 or 15, or a sequence that is 90% identical to SEQ ID NO: 3, 6, 9, 12 or 15, wherein the one or more polymorphisms in the genomic region encoding the polypeptide or in the regulatory region controlling expression of the polypeptide is associated with drought tolerance; and (b) identifying one or more alleles at the one or more polymorphisms that are associated with drought tolerance, wherein the one or more alleles associated with drought tolerance is used for marker assisted selection of a rice plant with drought tolerance, the one or more polymorphisms is in the coding region of the polynucleotide, and the regulatory region is a promoter.

BRIEF DESCRIPTION OF THE SEQUENCE LISTING

The disclosure can be more fully understood from the following detailed description and Sequence Listing which form a part of this application.

TABLE 1

SEQ ID NOs for nucleotide and amino acid sequences provided in the sequence listing

| Source species | Sequence Description | SEQ ID NO: (Nucleotide) | SEQ ID NO: (Amino Acid) |
|---|---|---|---|
| Oryza sativa | OsHDA14 | 1, 2 | 3 |
| Oryza sativa | OsZCW7 | 4, 5 | 6 |
| Oryza sativa | OsCCS1 | 7, 8 | 9 |
| Oryza sativa | OsDN-DTP10 | 10, 11 | 12 |
| Oryza sativa | OsDN-DTP11 | 13, 14 | 15 |
| Artificial | Primers | 16-35 | n/a |

The Sequence List contains the one-letter code for nucleotide sequences and the three-letter code for amino acid sequences as defined in conformity with the IUPAC-IUBMB standards described in Nucleic Acids Res. 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. § 1.822. The official copy of the sequence listing is submitted electronically via EFS-Web as an ASCII formatted sequence listing with a file named RTS22593H-US-PCT_Sequence-Listing.txt created on 28 Apr. 2020 and having a size of 51 kilobytes and is filed concurrently with the specification. The sequence listing comprised in this ASCII formatted document is part of the specification and is herein incorporated by reference in its entirety.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

As used herein:

The term "OsHDA14 (histone deacetylase 14)" refers to a rice polypeptide that confers drought tolerance phenotype and is encoded by the rice gene locus LOC_Os12g08220.1 and any associated allelic variants thereof. "HDA14 polypeptide" refers herein to the OsHDA14 polypeptide and its homologs from other organisms.

The OsHDA14 polypeptide (SEQ ID NO: 3) is encoded by the coding sequence (CDS) (SEQ ID NO: 2) or nucleotide sequence (SEQ ID NO: 1) at rice gene locus LOC_Os12g08220.1 and any associated allelic variants thereof. This polypeptide is annotated as "histone deacetylase, putative, expressed" in TIGR (the internet at plant biology msu.edu/index.shtml) and is annotated as "histone deacetylase 14 isoform X1" in NCBI (on the world web at ncbi.nlm.nih.gov), however does not have any prior assigned function.

The term "OsZCW7" refers to a rice polypeptide that confers drought tolerance and is encoded by the rice gene locus LOC_Os01g41000.1 and any associated allelic variants thereof. "ZCVV7 polypeptide" refers herein to the OsZCW7 polypeptide and its homologs from other organisms.

The OsZCW7 polypeptide (SEQ ID NO: 6) is encoded by the coding sequence (CDS) (SEQ ID NO: 5) or nucleotide sequence (SEQ ID NO: 4) at rice gene locus LOC_Os01g41000.1 and any associated allelic variants thereof. This polypeptide is annotated as "ZCW7, putative, expressed-Cloned seq" in TIGR and "hypothetical protein" in NCBI, however does not have any prior assigned function.

The term "OsCCS1 (condensin complex subunit 1)" refers to a rice polypeptide that confers drought tolerance and is encoded by the rice gene locus LOC_Os07g46540.1 and any associated allelic variants thereof. "CCS1 polypeptide" refers herein to the OsCCS1 polypeptide and its homologs from other organisms.

The OsCCS1 polypeptide (SEQ ID NO: 9) is encoded by the coding sequence (CDS) (SEQ ID NO: 8) or nucleotide sequence (SEQ ID NO: 7) at rice gene locus LOC_Os07g46540.1 and any associated allelic variants thereof. This polypeptide is annotated as "condensin complex subunit 1, putative, expressed" in TIGR.

The term "OsDN-DTP10 (drought tolerance protein 10)" refers to a rice polypeptide that confers drought tolerance phenotype and is encoded by the rice gene locus LOC_Os08g02260.1 and any associated allelic variants thereof. "DN-DTP10 polypeptide" refers herein to the OsDN-DTP10 polypeptide and its homologs from other organisms.

The OsDN-DTP10 polypeptide (SEQ ID NO: 12) is encoded by the coding sequence (CDS) (SEQ ID NO: 11) or nucleotide sequence (SEQ ID NO: 10) at rice gene locus LOC_Os08g02260.1 and any associated allelic variants thereof. This polypeptide is annotated as "expressed protein" in TIGR.

The term "OsDN-DTP11 (drought tolerance protein 11)" refers to a rice polypeptide that confers drought tolerance and is encoded by the rice gene locus LOC_Os07g36580.1 and any associated allelic variants thereof. "DN-DTP11 polypeptide" refers herein to the OsDN-DTP11 polypeptide and its homologs from other organisms.

The OsDN-DTP11 polypeptide (SEQ ID NO: 15) is encoded by the coding sequence (CDS) (SEQ ID NO: 14) or nucleotide sequence (SEQ ID NO: 13) at rice gene locus LOC_Os07g36580.1 and any associated allelic variants thereof. This polypeptide is annotated as "expressed protein" in TIGR.

The terms "monocot" and "monocotyledonous plant" are used interchangeably herein. A monocot of the current disclosure includes plants of the Gramineae family.

The terms "dicot" and "dicotyledonous plant" are used interchangeably herein. A dicot of the current disclosure includes the following families: Brassicaceae, Leguminosae, and Solanaceae.

"Plant" includes reference to whole plants, plant organs, plant tissues, seeds and plant cells and progeny of the same. Plant cells include, without limitation, cells from seeds, suspension cultures, embryos, meristematic regions, callus tissues, leaves, roots, shoots, gametophytes, sporophytes, pollen, and microspores.

"Progeny" comprises any subsequent generation of a plant.

"Heterologous" with respect to sequence means a sequence that originates from a foreign species, or, if from the same species, is substantially modified from its native form in composition and/or genomic position by deliberate human intervention.

"Transgenic" refers to any cell, cell line, callus, tissue, plant part or plant, the genome of which has been altered by the presence of a heterologous nucleic acid, such as a recombinant DNA construct.

A "control" or "control plant" or "control plant cell" provides a reference point for measuring changes in phenotype of a subject plant or plant cell in which genetic alteration, such as transformation, has been affected as to a gene of interest. A subject plant or plant cell may be descended from a plant or cell so altered and will comprise the alteration.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to a condition or stimulus that would induce expression of the gene of interest; or (e) the subject plant or plant cell itself, under conditions in which the gene of interest is not expressed. A control may comprise numerous individuals representing one or more of the categories above; for example, a collection of the non-transformed segregants of category "c" is often referred to as a bulk null.

In this disclosure, ZH11-TC and DP0158 may be designated as control plants, ZH11-TC represents rice plants generated from tissue cultured Zhonghua 11 and DP0158 represent plants transformed with empty vector of DP0158.

The term "trait" refers to a physiological, morphological, biochemical, or physical characteristic of a plant or particular plant material or cell.

"Phenotype" means the detectable characteristics of a cell or organism.

"Drought" refers to a decrease in water availability to a plant that, especially when prolonged or when occurring during critical growth periods, can cause damage to the plant or prevent its successful growth (e.g., limiting plant growth or seed yield).

"Drought tolerance" reflects a plant's ability to survive under drought conditions without exhibiting substantial physiological or physical deterioration, and/or its ability to recover when water is restored following a period of drought.

"Drought tolerance activity" of a polypeptide indicates that increased expression of the polypeptide in a transgenic plant confers increased drought tolerance of the transgenic plant relative to a reference or control plant.

"Increased drought tolerance" of a plant is measured relative to a reference or control plant, and reflects ability of the plant to survive under drought conditions with less physiological or physical deterioration than a reference or control plant grown under similar drought conditions, or ability of the plant to recover more substantially and/or more quickly than a control plant when water is restored following a period of drought.

"Environmental conditions" refer to conditions under which the plant is grown, such as the availability of water, availability of nutrients, or the presence of insects or disease.

"Paraquat" (1,1-dimethyl-4,4-bipyridinium dichloride), is a foliar-applied and non-selective bipyridinium herbicides, and causes photooxidative stress which further cause damage to plant or prevent its successful growth.

"Paraquat tolerance" is a trait of a plant, reflects the ability to survive and/or grow better when treated with Paraquat solution, compared to a reference or control plant.

"Increased paraquat tolerance" of a plant is measured relative to a reference or control plant, and reflects ability of the plant to survive with less physiological or physical deterioration than a reference or control plant after treated with paraquat solution. In general, tolerance to relative low level of paraquat can be used as a marker of abiotic stress tolerance, such as drought tolerance.

"Oxidative stress" reflects an imbalance between the systemic manifestation of reactive oxygen species and a biological system's ability to readily detoxify the reactive intermediates or to repair the resulting damage. Disturbances in the normal redox state of cells can cause toxic effects through the production of peroxides and free radicals that damage all components of the cell, including proteins, lipids, and DNA.

"Genome" as it applies to plant cells encompasses not only chromosomal DNA found within the nucleus, but also organelle DNA found within subcellular components (e.g., mitochondria, plastid) of the cell.

The terms "full complement" and "full-length complement" are used interchangeably herein, and refer to a complement of a given nucleotide sequence, wherein the complement and the nucleotide sequence consist of the same number of nucleotides and are 100% complementary.

"Polynucleotide", "nucleic acid sequence", "nucleotide sequence", and "nucleic acid fragment" are used interchangeably and refer to a polymer of RNA or DNA that is single- or double-stranded, optionally containing synthetic, non-natural or altered nucleotide bases.

"Polypeptide", "peptide", "amino acid sequence" and "protein" are used interchangeably herein to refer to a polymer of amino acid residues. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Mature" protein refers to a post-translationally processed polypeptide; i.e., any pre- or pro-peptides present in the primary translation product has been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterogonous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory elements and coding sequences that are derived from different sources, or regulatory elements and coding sequences derived from the same source, but arranged in a manner different than that normally found in nature.

"Regulatory elements" refer to nucleotide sequences located upstream (5' non-coding sequences), within, or downstream (3' non-coding sequences) of a coding sequence, and influencing the transcription, RNA processing or stability, or translation of the associated coding sequence. Regulatory elements may include, but are not limited to, promoters, translation leader sequences, introns, and polyadenylation recognition sequences. The terms "regulatory sequence" and "regulatory element" and "regulatory region" are used interchangeably herein.

"Promoter" refers to a nucleic acid fragment capable of controlling transcription of another nucleic acid fragment.

"Promoter functional in a plant" is a promoter capable of controlling transcription of genes in plant cells whether or not its origin is from a plant cell.

"Tissue-specific promoter" and "tissue-preferred promoter" may refer to a promoter that is expressed predominantly but not necessarily exclusively in one tissue or organ, but that may also be expressed in one specific cell or cell type.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance.

"Transient transformation" refers to the introduction of a nucleic acid fragment into the nucleus, or DNA-containing organelle, of a host organism resulting in gene expression without genetically stable inheritance.

An "allele" is one of two or more alternative forms of a gene occupying a given locus on a chromosome. When the alleles present at a given locus on a pair of homologous chromosomes in a diploid plant are the same, that plant is homozygous at that locus. If the alleles present at a given locus on a pair of homologous chromosomes in a diploid plant differ, that plant is heterozygous at that locus. If a transgene is present on one of a pair of homologous chromosomes in a diploid plant, that plant is hemizygous at that locus.

A "gene" refers to a nucleic acid fragment that expresses a functional molecule such as, but not limited to, a specific protein, including regulatory sequences preceding (5' non-coding sequences) and following (3' non-coding sequences) the coding sequence. "Native gene" refers to a gene as found in nature with its own regulatory sequences.

A "genomic locus" as used herein, generally refers to the location on a chromosome of the plant where a gene, such as a polynucleotide encoding a polypeptide described herein, is found.

A "mutated gene" is a gene that has been altered through human intervention. Such a "mutated gene" has a sequence that differs from the sequence of the corresponding non-mutated gene by at least one nucleotide addition, deletion, or substitution.

As "targeted mutation" is a mutation in a native gene that was made by altering a target sequence within the native gene. A targeted mutation can be introduced using any method known in the art or disclosed herein, such as, for example a method involving a double-strand-break-inducing agent that is capable of inducing a double-strand break in the DNA of the target sequence.

"Genetic modification" refers to a change or alteration in the genomic nucleic acid sequence of a plant introduced by deliberate human activity.

A "nuclear localization signal" is a signal peptide which directs the protein to the nucleus (Raikhel. (1992) *Plant Phys.* 100:1627-1632).

"CRISPR-associated genes" refers to nucleic acid sequences that encode polypeptide components of clustered regularly interspersed short palindromic repeats (CRISPR)-associated systems (Cas), and the genes are generally coupled, associated or close to or in the vicinity of flanking CRISPR loci. The terms "Cas gene", "CRISPR-associated gene" are used interchangeably herein. Examples include, but are not limited to, Cas3 and Cas9, which encode endonucleases from the CRISPR type I and type II systems, respectively.

"Cas endonuclease" refers to a Cas protein encoded by a Cas gene, wherein said Cas protein is capable of introducing a double strand break into a DNA target sequence. The Cas endonuclease is guided by the guide polynucleotide to recognize and optionally introduce a double strand break at a specific target site into the genome of a cell (U.S. 2015/0082478).

"Guide RNA (gRNA)" refers to a crRNA (CRISPR RNA): tracrRNA fused hybrid RNA molecule encoded by a customizable DNA element that, generally, comprises a copy of a spacer sequence which is complementary to the protospacer sequence of the genomic target site, and a binding domain for an associated-Cas endonuclease of the CRISPR complex.

"Guide polynucleotide" refers to a polynucleotide sequence that can form a complex with a Cas endonuclease and enables the Cas endonuclease to recognize and optionally cleave a DNA target site. The guide polynucleotide can be comprised of a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-0-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA".

The term "guide polynucleotide/Cas endonuclease system" refers to a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA, but only if the correct protospacer-adjacent motif (PAM) is approximately oriented at the 3' end of the target sequence.

"Genomic target site" refers to a protospacer and a protospacer adjacent motif (PAM) located in a host genome selected for targeted mutation and/or double-strand break.

"Protospacer" refers to a short DNA sequence (12 to 40 bp) that can be targeted for mutation, and/or double-strand break, mediated by enzymatic cleavage with a CRISPR system endonuclease guided by complementary base-pairing with the spacer sequence in the crRNA or sgRNA.

"Protospacer adjacent motif (PAM)" includes a 3 to 8 bp sequence immediately adjacent to the protospacer sequence in the genomic target site.

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

CRISPR loci (Clustered Regularly Interspaced Short Palindromic Repeats) (also known as SPIDRs-SPacer Interspersed Direct Repeats) constitute a family of recently described DNA loci. CRISPR loci consist of short and highly conserved DNA repeats (typically 24 to 40 bp, repeated from 1 to 140 times—also referred to as CRISPR-repeats) which are partially palindromic. The repeated sequences (usually specific to a species) are interspaced by variable sequences of constant length (typically 20 to 58 bp by depending on the CRISPR locus (WO2007/025097 published Mar. 1, 2007).

Endonucleases are enzymes that cleave the phosphodiester bond within a polynucleotide chain, and include restriction endonucleases that cleave DNA at specific sites without damaging the bases. Restriction endonucleases include Type I, Type II, Type III, and Type IV endonucleases, which further include subtypes. In the Type I and Type III systems, both the methylase and restriction activities are contained in a single complex. Endonucleases also include meganucleases, also known as homing endonucleases (HEases), which like restriction endonucleases, bind and cut at a specific recognition site, however the recognition sites for meganucleases are typically longer, about 18 bp or more (patent application WO-PCT PCT/US12/30061 filed on Mar. 22, 2012). Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates.

TAL effector nucleases are a new class of sequence-specific nucleases that can be used to make double-strand breaks at specific target sequences in the genome of a plant or other organism. TAL effector nucleases are created by fusing a native or engineered transcription activator-like (TAL) effector, or functional part thereof, to the catalytic domain of an endonuclease, such as, Foki. The unique, modular TAL effector DNA binding domain allows for the design of proteins with potentially any given DNA recognition specificity (Miller et al. (2011) Nature Biotechnology 29:143-148). Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs consist of an engineered DNA-binding zinc finger domain linked to a non-specific endonuclease domain, for example nuclease domain from a Type IIs endonuclease such as Fokl. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

The terms "target site", "target sequence", "target DNA", "target locus", "genomic target site", "genomic target sequence", and "genomic target locus" are used interchangeably herein and refer to a polynucleotide sequence in the genome (including choloroplastic and mitochondrial DNA) of a plant cell at which a double-strand break is induced in the plant cell genome by a Cas endonuclease. The target site can be an endogenous site in the plant genome, or alternatively, the target site can be heterologous to the plant and thereby not be naturally occurring in the genome, or the target site can be found in a heterologous genomic location compared to where it occurs in nature. As used herein, terms "endogenous target sequence" and "native target sequence" are used interchangeable herein to refer to a target sequence that is endogenous or native to the genome of a plant and is at the endogenous or native position of that target sequence in the genome of the plant.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST®, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

Turning now to the embodiments:

Embodiments include isolated polynucleotides and polypeptides, and recombinant DNA constructs useful for conferring drought tolerance; compositions (such as plants or seeds) comprising these recombinant DNA constructs; and methods utilizing these recombinant DNA constructs.

Isolated Polynucleotides and Polypeptides:

The present disclosure includes the following isolated polynucleotides and polypeptides:

An isolated polynucleotide comprising: (i) a nucleic acid sequence encoding a polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3, 6, 9, 12 or 15; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs of the present disclosure. In certain embodiments, an increased expression of the encoded polypeptide increases plant drought tolerance, and/or paraquat tolerance activity. In certain embodiments, an increased expression of the encoded polypeptide increases plant grain yield under normal conditions.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3, 6, 9, 12 or 15. The polypeptide is preferably a drought tolerance polypeptide. In certain embodiments, an increased expression of the polypeptide increases plant drought tolerance and/or paraquat tolerance activity. In certain embodiments, an increased expression of the encoded polypeptide increases plant grain yield under normal conditions.

An isolated polynucleotide comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO:1, 2, 4, 5, 7, 8, 10, 11, 13 or 14; or (ii) a full complement of the nucleic acid sequence of (i). Any of the foregoing isolated polynucleotides may be utilized in any recombinant DNA constructs of the present disclosure. The isolated polynucleotide preferably encodes a drought tolerance polypeptide. In certain embodiments, an increased expression of the polynucleotide improves plant drought tolerance and/or paraquat tolerance activity. In certain embodiments, an increased expression of the polynucleotide increases plant grain yield under normal conditions.

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Recombinant DNA Constructs:

In one aspect, the present disclosure includes recombinant DNA constructs.

In one embodiment, a recombinant DNA construct comprises a polynucleotide operably linked to at least one regulatory element (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3, 6, 9, 12 or 15; or (ii) a full complement of the nucleic acid sequence of (i).

In another embodiment, a recombinant DNA construct comprises a polynucleotide operably linked to at least one regulatory element (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, 2, 4, 5, 7, 8, 10, 11, 13 or 14; or (ii) a full complement of the nucleic acid sequence of (i).

In another embodiment, a recombinant DNA construct comprises a polynucleotide operably linked to at least one regulatory element (e.g., a promoter functional in a plant), wherein said polynucleotide encodes a HDA14, ZCW7, CCS1, DN-DTP10, DN-DTP11 polypeptide. The polypeptide preferably has drought tolerance and/or paraquat tolerance activity. The polynucleotide may be from, for example, *Oryza sativa*, *Arabidopsis thaliana*, *Zea mays*, *Glycine max*, *Glycine tabacina*, *Glycine soja* or *Glycine tomentella*.

Regulatory Elements:

A recombinant DNA construct of the present disclosure may comprise at least one regulatory element.

A regulatory element may be a promoter, enhancer, 5'UTR, or 3'UTR.

A number of promoters can be used in recombinant DNA constructs of the present disclosure. The promoters can be selected based on the desired outcome, and may include constitutive, tissue-specific, inducible, or other promoters for expression in the host organism.

Promoters that cause a gene to be expressed in most cell types at most times are commonly referred to as "constitutive promoters".

High-level, constitutive expression of the candidate gene under control of the 35S or UBI promoter may (or may not) have pleiotropic effects, although candidate gene efficacy may be estimated when driven by a constitutive promoter. Use of tissue-specific and/or stress-induced promoters may eliminate undesirable effects but retain the ability to enhance drought tolerance. This effect has been observed in *Arabidopsis* (Kasuga et al. (1999) *Nature Biotechnol.* 17:287-91).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, those discussed in U.S. Pat. Nos. 5,608,149; 5,608,144; 5,604,121; 5,569, 597; 5,466,785; 5,399,680; 5,268,463; 5,608,142; and 6,177,611.

In choosing a promoter to use in the methods of the disclosure, it may be desirable to use a tissue-specific or developmentally regulated promoter.

A tissue-specific or developmentally-regulated promoter is a DNA sequence which regulates the expression of a DNA sequence selectively in the cells/tissues of a plant, such as in those cells/tissues critical to tassel development, seed set, or both, and which usually limits the expression of such a DNA sequence to the developmental period of interest (e.g. tassel development or seed maturation) in the plant. Any identifiable promoter which causes the desired temporal and spatial expression may be used in the methods of the present disclosure.

For the expression of a polynucleotide in developing seed tissue, promoters of particular interest include seed-preferred promoters, particularly early kernel/embryo promoters and late kernel/embryo promoters. Kernel development post-pollination is divided into approximately three primary phases. The lag phase of kernel growth occurs from about 0 to 10-12 DAP. During this phase the kernel is not growing significantly in mass, but rather important events are being carried out that will determine kernel vitality (e.g., number of cells established). The linear grain fill stage begins at about 10-12 DAP and continues to about 40 DAP. During this stage of kernel development, the kernel attains almost all of its final mass, and various storage products (i.e., starch, protein, oil) are produced. Finally, the maturation phase occurs from about 40 DAP to harvest. During this phase of kernel development the kernel becomes quiescent and begins to dry down in preparation for a long period of dormancy prior to germination. As defined herein "early kernel/embryo promoters" are promoters that drive expression principally in developing seed during the lag phase of development (i.e., from about 0 to about 12 DAP). "Late kernel/embryo promoters", as defined herein, drive expression principally in developing seed from about 12 DAP through maturation. There may be some overlap in the window of expression. The choice of the promoter will depend on the ABA-associated sequence utilized and the phenotype desired.

Early kernel/embryo promoters include, for example, Cim1 that is active 5 DAP in particular tissues (WO 00/11177), which is herein incorporated by reference. Other early kernel/embryo promoters include the seed-preferred promoters end1 which is active 7-10 DAP, and end2, which is active 9-14 DAP in the whole kernel and active 10 DAP in the endosperm and pericarp (WO 00/12733), herein incorporated by reference. Additional early kernel/embryo promoters that find use in certain methods of the present disclosure include the seed-preferred promoter Itp2 (U.S. Pat. No. 5,525,716); maize Zm40 promoter (U.S. Pat. No. 6,403,862); maize nuc1c (U.S. Pat. No. 6,407,315); maize ckx1-2 promoter (U.S. Pat. No. 6,921,815 and US Patent Application Publication Number 2006/0037103); maize lec1 promoter (U.S. Pat. No. 7,122,658); maize ESR promoter (U.S. Pat. No. 7,276,596); maize ZAP promoter (U.S. Patent Application Publication Numbers 20040025206 and 20070136891); maize promoter eep1 (U.S. Patent Application Publication Number 20070169226); and maize promoter ADF4 (U.S. Patent Application No. 60/963,878, filed 7 Aug. 2007).

Additional promoters for regulating the expression of the nucleotide sequences of the present disclosure in plants are stalk-specific promoters, including the alfalfa S2A promoter (GenBank Accession No. EF030816; Abrahams et al. (1995) *Plant Mol. Biol.* 27:513-528) and S2B promoter (GenBank Accession No. EF030817) and the like, herein incorporated by reference.

Promoters for use in certain embodiments of the current disclosure may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (Genbank accession number EF030817), and the constitutive promoter GOS2 from *Zea mays*; root preferred promoters, such as the maize NAS2 promoter, the maize Cyclo promoter (US 2006/0156439, published Jul. 13, 2006), the maize ROOTMET2 promoter (WO05063998, published Jul. 14, 2005), the CR1B10 promoter (WO06055487, published May 26, 2006), the CRWAQ81 (WO05035770, published Apr. 21, 2005) and the maize ZRP2.47 promoter (NCBI accession number: U38790; GI No. 1063664).

Recombinant DNA constructs of the present disclosure may also include other regulatory elements, including but not limited to, translation leader sequences, introns, and polyadenylation recognition sequences. In certain embodiments, a recombinant DNA construct further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg. (1988) *Mol. Cell Biol.* 8:4395-4405; Callis et al. (1987) *Dev.* 1:1183-1200).

An enhancer or enhancer element refers to a cis-acting transcriptional regulatory element, a.k.a. cis-element, which confers an aspect of the overall expression pattern, but is usually insufficient alone to drive transcription, of an operably linked polynucleotide sequence. An isolated enhancer element may be fused to a promoter to produce a chimeric promoter cis-element, which confers an aspect of the overall modulation of gene expression. Enhancers are known in the art and include the SV40 enhancer region, the CaMV 35S enhancer element, and the like. Some enhancers are also known to alter normal regulatory element expression patterns, for example, by causing a regulatory element to be expressed constitutively when without the enhancer, the same regulatory element is expressed only in one specific tissue or a few specific tissues. Duplicating the upstream region of the CaMV35S promoter has been shown to increase expression by approximately tenfold (Kay, R. et al., (1987) Science 236: 1299-1302).

Compositions:

In hybrid seed propagated crops, mature transgenic plants or genome edited plants can be self-pollinated to produce a homozygous inbred plant. The inbred plant produces seed containing the newly introduced recombinant DNA construct. These seeds can be grown to produce plants that would exhibit an altered agronomic characteristic (e.g., an increased agronomic characteristic optionally under water limiting conditions), or used in a breeding program to produce hybrid seed, which can be grown to produce plants that would exhibit such an altered agronomic characteristic. The seeds may be maize seeds or rice seeds.

The plant may be a monocotyledonous or dicotyledonous plant, for example, a rice or maize or soybean plant, such as a maize hybrid plant or a maize inbred plant. The plant may also be sunflower, sorghum, canola, wheat, alfalfa, cotton, barley, millet, sugar cane or switchgrass.

The recombinant DNA construct may be stably integrated into the genome of the plant.

Particular embodiments include but are not limited to the following:

1. A transgenic or genome edited plant (for example, a rice or maize or soybean plant) comprising in its genome a polynucleotide operably linked to at least one regulatory element, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity, to SEQ ID NO: 3, 6, 9, 12 or 15, and wherein said plant exhibits increased drought tolerance and/or paraquat tolerance when compared to a control plant.

2. A transgenic plant (for example, a rice or maize or soybean plant) comprising in its genome a recombinant DNA construct comprising a polynucleotide operably linked to at least one regulatory element, optionally a heterologous regulatory element, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity, to SEQ ID NO: 3, 6, 9, 12 or 15, and wherein said plant exhibits increased drought tolerance and/or paraquat tolerance when compared to a control plant.

3. A genome edited plant (for example, a rice or maize or soybean plant) comprising a targeted genetic modification at a genomic locus that encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity, to SEQ ID NO: 3, 6, 9, 12 or 15, wherein said plant exhibits increased drought tolerance and/or paraquat tolerance when compared to a control plant.

4. Any progeny of the above plants in embodiment 1-3, any seeds of the above plants in embodiment 1-3, any seeds of progeny of the above plants in embodiment 1-3, and cells from any of the above plants in embodiment 1-3 and progeny thereof.

In any of the foregoing embodiment 1-4 or other embodiments, the drought tolerance polypeptide may be from *Oryza sativa, Oryza australiensis, Oryza barthii, Oryza glaberrima* (African rice), *Oryza latifolia, Oryza longistaminata, Oryza meridionalis, Oryza officinalis, Oryza punctata, Oryza rufipogon* (brownbeard or red rice), *Oryza nivara* (Indian wild rice), *Arabidopsis thaliana, Zea mays, Glycine max, Glycine tabacina, Glycine soja* or *Glycine tomentella*.

In any of the foregoing embodiment 1, 2, or 4 or other embodiments, the recombinant DNA construct may comprise at least a promoter functional in a plant as a regulatory element.

In any of the foregoing embodiment 1-4 or other embodiments, the plant may exhibit the alteration of at least one agronomic characteristic when compared, under water limiting conditions, to a control plant.

In any of the foregoing embodiment 1-4 or other embodiments, the plant may exhibit the alteration of at least one agronomic characteristic when compared, under oxidative stress (paraquat) conditions, to a control plant.

The Examples below describe some representative protocols and techniques for simulating drought conditions and/or evaluating drought tolerance; simulating oxidative conditions.

One can also evaluate drought tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring drought conditions (e.g., by measuring for substantially equivalent yield under drought conditions compared to non-drought conditions, or by measuring for less yield loss under drought conditions compared to yield loss exhibited by a control or reference plant).

Parameters such as recovery degree, survival rate, paraquat tolerance rate, gene expression level, water use efficiency, level or activity of an encoded protein, and others are typically presented with reference to a control cell or control plant.

One of ordinary skill in the art would readily recognize a suitable control or reference plant to be utilized when assessing or measuring an agronomic characteristic or phenotype of a transgenic plant using compositions or methods as described herein. For example, by way of non-limiting illustrations:

1. Progeny of a transformed plant which is hemizygous with respect to a recombinant DNA construct, such that the progeny are segregating into plants either comprising or not comprising the recombinant DNA construct: the progeny comprising the recombinant DNA construct would be typically measured relative to the progeny not comprising the recombinant DNA construct. The progeny not comprising the recombinant DNA construct is the control or reference plant.

2. Introgression of a recombinant DNA construct into an inbred line, such as in rice and maize, or into a variety, such as in soybean: the introgressed line would typically be measured relative to the parent inbred or variety line (i.e., the parent inbred or variety line is the control or reference plant).

3. Two hybrid lines, wherein the first hybrid line is produced from two parent inbred lines, and the second hybrid line is produced from the same two parent inbred lines except that one of the parent inbred lines contains a recombinant DNA construct: the second hybrid line would typically be measured relative to the first hybrid line (i.e., the first hybrid line is the control or reference plant).

4. A plant comprising a recombinant DNA construct: the plant may be assessed or measured relative to a control plant not comprising the recombinant DNA construct but otherwise having a comparable genetic background to the plant (e.g., sharing at least 90%, 91%, 92%, 93%, 94%, 95%, 96%, 97%, 98%, 99%, or 100% identity of nuclear genetic material compared to the plant comprising the recombinant DNA construct).

Methods:

Methods include but are not limited to methods for increasing drought tolerance in a plant, methods for evaluating drought tolerance in a plant, methods for increasing paraquat tolerance, methods for altering an agronomic characteristic in a plant, methods for determining an alteration of an agronomic characteristic in a plant, and methods for producing seed.

Methods include but are not limited to the following:

A method for transforming a cell comprising transforming a cell with any one or more of the isolated polynucleotides of the present disclosure, wherein, in particular embodiments, the cell is eukaryotic cell, e.g., a yeast, insect or plant cell; or prokaryotic cell, e.g., a bacterial cell.

A method for producing a transgenic plant comprising transforming a plant cell with any of the isolated polynucleotides or recombinant DNA constructs of the present disclosure and regenerating a transgenic plant from the transformed plant cell, wherein, the transgenic plant and the transgenic seed obtained by this method may be used in other methods of the present disclosure.

A method for isolating a polypeptide of the disclosure from a cell or culture medium of the cell, wherein the cell comprises a recombinant DNA construct comprising a polynucleotide of the disclosure operably linked to at least one regulatory element, and wherein the transformed host cell is grown under conditions that are suitable for expression of the recombinant DNA construct.

A method for altering the level of expression of a polypeptide of the disclosure in a host cell comprising: (a) transforming a host cell with a recombinant DNA construct of the present disclosure; and (b) growing the transformed host cell under conditions that are suitable for the expression of the recombinant DNA construct, wherein the expression of the recombinant DNA construct results in production of altered levels of the polypeptide of the disclosure in the transformed host cell.

One embodiment provides a method of increasing drought tolerance in a plant, comprising increasing the expression of at least one polynucleotide encoding a polypeptide with amino acid sequence of at least 90% identity to SEQ ID NO: 3, 6, 9, 12 or 15.

One embodiment provides a method of increasing drought tolerance and/or paraquat tolerance in a plant, comprising: (a) introducing into a regenerable plant cell a recombinant DNA construct comprising a polynucleotide operably linked to at least one regulatory element (for example, a promoter functional in a plant), wherein the polynucleotide encodes a polypeptide having an amino acid sequence of at least 90%, 91%, 92%, 93%, 94%, 95%, 96%, 97%, 98%, 99%, or 100% identity to SEQ ID NO: 3, 6, 9, 12 or 15; (b) generating a transgenic plant from the regenerable plant cell after step (a), wherein the transgenic plant comprises in its genome the recombinant DNA construct and exhibits increased drought tolerance and/or paraquat tolerance when compared to a control plant; and further (c) obtaining a progeny plant derived from transgenic plant, wherein said progeny plant comprises in its genome the recombinant DNA construct and exhibits increased drought tolerance and/or paraquat tolerance when compared to a control plant.

One embodiment provides a method of increasing drought tolerance and/or paraquat tolerance in a plant, comprising: (a) introducing into a regenerable plant cell a targeted genetic modification at a genomic locus that encodes a polypeptide comprising an amino acid sequence having at least 90%, 91%, 92%, 93%, 94%, 95%, 96%, 97%, 98%, 99%, or 100% identity to SEQ ID NO: 3, 6, 9, 12 or 15; and (b) generating the plant, wherein the level and/or activity of the encoded polypeptide is increased in the plant.

A method of evaluating drought tolerance and/or paraquat tolerance in a plant comprising (a) obtaining a transgenic or genome edited plant, which comprises in its genome a polynucleotide operably linked to at least one regulatory element, optionally a heterologous regulatory element (for example, a promoter functional in a plant), wherein said polynucleotide encodes a polypeptide having an amino acid sequence of at least 90%, 91%, 92%, 93%, 94%, 95%, 96%, 97%, 98%, 99%, or 100% identity, to SEQ ID NO: 3, 6, 9, 12 or 15; (b) obtaining a progeny plant derived from said transgenic or genome edited plant, wherein the progeny plant comprises in its genome the recombinant DNA construct; and (c) evaluating the progeny plant for drought tolerance and/or paraquat tolerance compared to a control plant.

A method of determining an alteration of an agronomic characteristic in a plant comprising (a) obtaining a transgenic or genome edited plant which comprises in its genome a polynucleotide operably linked to at least one regulatory element, optionally a heterologous regulatory element (for example, a promoter functional in a plant), wherein said polynucleotide encodes a polypeptide having an amino acid sequence of at least 90%, 91%, 92%, 93%, 94%, 95%, 96%, 97%, 98%, 99%, or 100% identity when compared to SEQ ID NO: 3, 6, 9, 12 or 15; (b) obtaining a progeny plant derived from said transgenic or genome edited plant; and (c) determining whether the progeny plant exhibits an alteration in at least one agronomic characteristic when compared, optionally under water limiting conditions to a control plant.

A method of producing seed comprising any of the preceding methods, and further comprising obtaining seeds from said progeny plant, wherein said seeds comprise in their genome said recombinant DNA construct.

The introduction of recombinant DNA constructs of the present disclosure into plants may be carried out by any suitable technique, including but not limited to direct DNA uptake, chemical treatment, electroporation, microinjection, cell fusion, infection, vector-mediated DNA transfer, bombardment, or *Agrobacterium*-mediated transformation. Techniques for plant transformation and regeneration have been described in International Patent Publication WO 2009/006276, the contents of which are herein incorporated by reference.

In addition, methods to modify or alter the host endogenous genomic DNA are available. This includes altering the host native DNA sequence or a pre-existing transgenic sequence including regulatory elements, coding and non-coding sequences. These methods are also useful in targeting nucleic acids to pre-engineered target recognition sequences in the genome. As an example, the genetically modified cell or plant described herein, is generated using "custom" engineered endonucleases such as meganucleases produced to modify plant genomes (e.g., WO 2009/114321; Gao et al. (2010) Plant Journal 1:176-187). Another site-directed engineering is through the use of zinc finger domain recognition coupled with the restriction properties of restriction enzyme (e.g., Urnov, et al. (2010) *Nat Rev Genet.* 11(9):636-46; Shukla, et al. (2009) *Nature* 459 (7245):437-41). A transcription activator-like (TAL) effector-DNA modifying enzyme (TALE or TALEN) is also used to engineer changes in plant genome. See e.g., US20110145940, Cermak et al., (2011) Nucleic Acids Res. 39(12) and Boch et al., (2009), Science 326 (5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The CRISPR/Cas system allows targeted cleavage of genomic DNA guided by a customizable small noncoding RNA.

The development or regeneration of plants containing the foreign, exogenous isolated nucleic acid fragment that encodes a protein of interest is well known in the art. The regenerated plants may be self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant containing a desired polypeptide is cultivated using methods well known to one skilled in the art.

Stacking of Traits

Modified plants may comprise a stack of one or more drought tolerance polynucleotides disclosed herein with one or more additional polynucleotides resulting in the production or suppression of multiple polypeptide sequences. Modified plants comprising stacks of polynucleotide sequences can be obtained by either or both of traditional breeding methods or through genetic engineering methods. These methods include, but are not limited to, breeding individual lines each comprising a polynucleotide of interest, genome editing, transforming a transgenic plant comprising a gene disclosed herein with a subsequent gene and cotransformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences.

EXAMPLES

Example 1

Cloning and Vector Construction of Drought Tolerance Genes

Primers were designed for cloning rice drought tolerance genes OsHDA14, OsZCW7, OsCCS1, OsDN-DTP10 and OsDN-DTP11. The primers and the expected-lengths of the amplified genes are shown in Table 2.

OsHDA14 cDNA was cloned using pooled cDNA from leaf, stem and root tissues of Zhonghua 11 plant as the template. OsZCVV7, OsCCS1, OsDN-DTP10 and OsDN-DTP11 gDNAs were cloned, and amplified using genomic DNA of Zhonghua 11 as the template.

construct of DP0999 and coding sequence of OsDN-DTP10 are provided as SEQ ID NO: 10 and 11, the encoded amino acid sequence of OsDN-DTP10 is shown in SEQ ID NO: 12; and the cloned nucleotide sequence in construct of DP1131 and coding sequence of OsDN-DTP11 are provided as SEQ ID NO: 13 and 14, the encoded amino acid sequence of OsDN-DTP11 is show in SEQ ID NO: 15.

Example 2

Generation of Rice Plants with Increased Gene Expression

The over-expression vectors and empty vector (DP0158) were transformed into the Zhonghua 11 (*Oryza sativa L.*) by *Agrobacteria*-mediated method as described by Lin and Zhang ((2005) *Plant Cell Rep.* 23:540-547). Zhonghua 11 was cultivated by the Institute of Crop Sciences, Chinese Academy of Agricultural Sciences. The first batch of seeds used in this research was provided by Beijing Weiming Kaituo Agriculture Biotech Co., Ltd. Calli induced from embryos was transformed with *Agrobacteria* with the vector. The transgenic seedlings (T0) generated in transformation laboratory are transplanted in the field to get T1 seeds. The T1 and T2 seeds are stored at cold room (4° C.). The over-expression vectors contain marker genes. T1 and T2

TABLE 2

Primers for cloning rice drought tolerance genes

| Primer | Sequence | SEQ ID NO: | Gene name | Length of amplified fragment (bp) |
|---|---|---|---|---|
| gc-5208 | 5'-GAGAGATAGATCCCTGGAGGTTTGCAG-3 | 16 | OsHDA14 | 1480 |
| gc-5209 | 5'-CTGGAAAGTGCAAAAGCTAACAAGACATG-3' | 17 | | |
| gc-6528 | 5'-CATGGGTGTGAGTATGGGGCAAG-3' | 18 | OsZCW7 | 684 |
| gc-6529 | 5'-GTTTGGCCTAGCAGCTTTCGATG-3' | 19 | | |
| gc-2423 | 5'-CCCATCCTTCTCTCTCTCCACCTAAG-3' | 20 | OsCCS1 | 7916 |
| gc-2424 | 5'-GAGTTGTTGCCACCTGGTCCATATTACAGTTC-3' | 21 | | |
| gc-6778 | 5'-GAGGTGGCGGAGTTTGTGGAG-3' | 22 | OsDN- | 635 |
| gc-6779 | 5'-CGGTTTAGGGGTGGATGGGATG-3' | 23 | DTP10 | |
| gc-6498 | 5'-CTGCTGAGGGGTAAGCGAAGTGTGGGGAAGTCTC-3' | 24 | OsDN- | 2443 |
| gc-6499 | 5'-CCGCTGAGGCTTCACCGCCCTCCTACTGCCTTC-3' | 25 | DTP11 | |

The PCR amplified products were extracted after the agarose gel electrophoresis using a column kit and then ligated with TA cloning vectors. The sequences and orientation in these constructs were confirmed by sequencing. Then these genes were cloned into plant binary construct DP0158 (pCAMBIA1300-DsRed).

The cloned nucleotide sequence in construct of DP0539 and coding sequence of OsHDA14 are provided as SEQ ID NO: 1 and 2, the encoded amino acid sequence of OsHDA14 is shown in SEQ ID NO: 3; the cloned nucleotide sequence in construct of DP0924 and coding sequence of OsZCW7 are provided as SEQ ID NO: 4 and 5, the encoded amino acid sequence of OsZCW7 is shown in SEQ ID NO: 6; the cloned nucleotide sequence in construct of DP0994 and coding sequence of OsCCS1 are provided as SEQ ID NO: 7 and 8, the encoded amino acid sequence of OsCCS1 is shown in SEQ ID NO: 9; the cloned nucleotide sequence in seeds which showed red color under green fluorescent light were transgenic seeds and were used in the following trait screening.

Example 3

Gene Expression Analysis

The gene expression levels in the transgenic rice plants were analyzed. A standard RT-PCR or a real-time RT-PCR procedure was used. EF-1α gene was used as an internal control to show that the amplification and loading of samples from the transgenic rice and the controls were similar. Gene expression was normalized based on the EF-1α mRNA levels.

The relative expression levels of OsHDA14 gene in leaves of different transgenic rice lines were determined by real-time PCR analyses. The base level of expression in ZH11-TC was set at 1.00, and the expression levels in other OsHDA14 lines increased from about 47-fold to 286-fold compared to ZH11-TC. ZH11-TC is tissue cultured ZH11 rice and DP0158 is empty vector transformed ZH11 rice plants. The primers for real-time RT-PCR for the OsHDA14 gene in the over-expression transgenic rice are listed below:

```
                                       (SEQ ID NO: 26)
DP0539-F1: 5'-CTACAACCTGGAGTCGCTG-3'

(SEQ ID NO: 27)
DP0539-R1: 5-TGCTTGGCCTTGTCGATG-3'
```

The relative expression levels of OsZCW7 gene in leaves of different transgenic rice lines were determined by real-time PCR analyses and increased from about 1275-fold to 3515-fold as compared to the base expression level in ZH11-TC (control; set at 1.00). OsZCW7 over-expressed in all the tested transgenic rice lines. The primers used for the real-time PCR are as below:

```
                                       (SEQ ID NO: 28)
DP0924-F1: 5'-TGTGAGGAAGATAGCGAAAAGG-3'

(SEQ ID NO: 29)
DP0924-R1: 5'-GATATCCTCGTCTCCGCAAAC-3'
```

The relative expression levels of OsCCS1 gene in leaves of different transgenic rice lines were determined by real-time PCR analyses and increased from about 2-fold to 135-fold as compared to the base expression level in ZH11-TC (control; set at 1.00). OsCCS1 over-expressed in all the transgenic lines.

```
                                       (SEQ ID NO: 30)
DP0994-F1: 5'-TGAAGATAAGGAGAACATGCCAG-3'

(SEQ ID NO: 31)
DP0994-R1: 5'-TCGCTGATTGAACCTCTGTG-3'
```

The relative expression levels of OsDN-DTP10 gene in leaves of different transgenic rice lines were determined by real-time PCR analyses and increased from about 1.8-fold to 10-fold as compared to the base expression level in ZH11-TC (control; set at 1.00). The expression levels of OsDN-DTP10 are higher than that in ZH11-TC seedlings.

```
                                       (SEQ ID NO: 32)
DP0999-F1: 5'-GAGCTCGCGAAGGTGGTG-3'

(SEQ ID NO: 33)
DP0999-R1: 5'-CAAACTCGTCCCACCTGG-3'
```

The relative expression levels of OsDN-DTP11 gene in leaves of different transgenic rice lines were determined by real-time PCR analyses and increased from about 2-fold to 186-fold as compared to the base expression level in ZH11-TC (control; set at 1.00).

```
                                       (SEQ ID NO: 34)
DP1131-F1: 5'-ACAGTAACCCGCTACATTATCG-3'

(SEQ ID NO: 35)
DP1131-R1: 5'-GACACGTCCTGCATTTTACTG-3'
```

Example 4

Grain Yield of Mature Transgenic Rice Plants Under Well-Watered Conditions

The transgenic rice plants and ZH11-TC and DP0158 rice plants were planted in the paddy field to measure the grain yield under the well-watered conditions. Five transgenic lines from each gene construct were chosen. The T2 seeds were first sterilized, and the germinated seeds were planted in a seedbed field. At 3-leaf stage, the seedlings were transplanted into the testing field with 4 replicates and 40 plants per replicate for each transgenic line, and the 4 replicates were planted in the same block. ZH11-TC and DP0158 seedlings were nearby the transgenic lines in the same block, and were used as controls in the statistical analysis.

The rice plants were managed by normal practice using pesticides and fertilizers. Plant phenotypes were observed and recorded during the experiments. At the end of the growing season, representative plants of each transgenic line were harvested from the middle of the row per line, and grain yield per plant was measured. The grain yield data were statistically analyzed using mixed linear model.

1) OsZCW7 (DP0924) Transgenic Rice Plants Planted under Well-Watered Conditions

Five OsZCW7 transgenic rice lines were used. There was no visibly different phenotype between the transgenic rice plants and the control plants. As shown in Table 3, the grain yield per plant of OsZCW7 transgenic rice was significantly greater than that of ZH11-TC and DP 0158 controls at the construct level, and all the transgenic rice lines showed greater grain yield per plant than controls at the line level. These results show that over-expression of OsZCW7 gene improves the grain yield per plant under well-watered conditions.

TABLE 3

Grain yield analysis of OsZCW7 transgenic rice plants under well-watered conditions

| Line ID | Number of survival plants | Number of harvested plants | Yield per Plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0924 (construct) | 897 | 685 | 21.30 | 5.78 | 0.000 | Y | 2.31 | 0.000 | Y |
| ZH11-TC | | | 15.52 | | | | | | |
| DP0158 | | | 18.99 | | | | | | |
| DP0924.04 | 180 | 138 | 20.60 | 5.08 | 0.000 | Y | 1.61 | 0.040 | Y |
| DP0924.05 | 180 | 138 | 21.53 | 6.01 | 0.000 | Y | 2.55 | 0.001 | Y |

TABLE 3-continued

Grain yield analysis of OsZCW7 transgenic rice plants under well-watered conditions

| Line ID | Number of survival plants | Number of harvested plants | Yield per Plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0924.07 | 177 | 134 | 22.19 | 6.66 | 0.000 | Y | 3.20 | 0.000 | Y |
| DP0924.09 | 180 | 137 | 20.70 | 5.17 | 0.000 | Y | 1.71 | 0.029 | Y |
| DP0924.15 | 180 | 138 | 21.49 | 5.97 | 0.000 | Y | 2.51 | 0.002 | Y |

2) OsCCS1 (DP0994) Transgenic Rice Plants Planted under Well-Watered Conditions

Five OsCCS1 transgenic rice lines were used. There was no visibly different phenotype between the transgenic rice plants and the control plants. As shown in Table 4, the grain yield per plant of OsCCS1 transgenic rice was significantly greater than that of ZH11-TC and DP0158 controls at the construct level, and three transgenic rice lines showed greater grain yield per plant than controls at the line level. These results show that over-expression of OsCCS1 gene may improve the grain yield per plant under well-watered conditions.

TABLE 4

Grain yield analysis of OsCCS1 transgenic rice plants under well-watered conditions

| Line ID | Number of survival plants | Number of harvested plants | Yield per Plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0994 (construct) | 717 | 530 | 28.95 | 1.46 | 0.023 | Y | 1.88 | 0.003 | Y |
| ZH11-TC | | | 27.49 | | | | | | |
| DP0158 | | | 27.07 | | | | | | |
| DP0994.03 | 144 | 119 | 35.32 | 7.83 | 0.000 | Y | 8.25 | 0.000 | Y |
| DP0994.04 | 144 | 95 | 31.00 | 3.51 | 0.003 | Y | 3.92 | 0.001 | Y |
| DP0994.08 | 142 | 79 | 28.59 | 1.10 | 0.431 | | 1.52 | 0.276 | |
| DP0994.09 | 143 | 117 | 24.20 | -3.29 | 0.005 | | -2.87 | 0.013 | |
| DP0994.11 | 144 | 120 | 25.67 | -1.82 | 0.119 | | -1.41 | 0.230 | |

3) OsDN-DTP11 (DP1131) Transgenic Rice Plants Planted under Well-Watered Conditions Five OsDN-DTP11 transgenic rice lines were used. There was no visibly different phenotype between the transgenic rice plants and the control plants. As shown in Table 5, the grain yield per plant of OsDN-DTP11 transgenic rice was significantly greater than that of ZH11-TC and DP 0158 controls at the construct level, and all the transgenic rice lines showed greater grain yield per plant than controls at the line level. These results show that over-expression of OsDN-DTP11 gene improves the grain yield per plant under well-watered conditions.

TABLE 5

Grain yield analysis of OsDN-DTP11 transgenic rice plants under well-watered conditions

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP1131 (Construct) | | | 21.98 | 6.46 | 0.000 | Y | 2.99 | 0.000 | Y |
| ZH11-TC | | | 15.52 | | | | | | |
| DP0158 | | | 18.99 | | | | | | |
| DP1131.01 | 180 | 137 | 22.17 | 6.65 | 0.000 | Y | 3.18 | 0.000 | Y |
| DP1131.02 | 180 | 133 | 21.77 | 6.25 | 0.000 | Y | 2.78 | 0.000 | Y |
| DP1131.03 | 180 | 137 | 20.58 | 5.06 | 0.000 | Y | 1.60 | 0.040 | Y |
| DP1131.06 | 179 | 137 | 22.70 | 7.17 | 0.000 | Y | 3.71 | 0.000 | Y |
| DP1131.08 | 175 | 128 | 22.69 | 7.17 | 0.000 | Y | 3.70 | 0.000 | Y |

Example 5

Field Drought Assays of Mature Transgenic Rice Plants

The transgenic rice plants were further tested under field drought conditions. For the Field drought assays of mature rice plants, 12 transgenic lines from each gene construct were tested. The T2 seeds were first sterilized, and the germinated seeds were planted in a seedbed field. At 3-leaf stage, the seedlings were transplanted into the testing field with 4 replicates and 10 plants per replicate for each transgenic line, and the 4 replicates were planted in the same block. ZH11-TC and DP0158 seedlings were nearby the transgenic lines in the same block, and were used as controls in the statistical analysis.

The rice plants were managed by normal practice using pesticides and fertilizers. Watering was stopped at the panicle initiation stage, so as to give drought stress at flowering stage depending on the weather conditions (temperature and humidity). The soil water content was measured every 4 days at about 10 sites per block using TDR30 (Spectrum Technologies, Inc.).

Plant phenotypes were observed and recorded during the experiments. The phenotypes include heading date, leaf rolling degree, drought sensitivity and drought tolerance. Special attention was paid to leaf rolling degree at noontime. At the end of the growing season, six representative plants of each transgenic line were harvested from the middle of the row per line, and grain yield per plant was measured. The grain yield data were statistically analyzed using mixed linear model. Positive transgenic lines were selected based on the analysis (P<0.1).

Field Drought (DRT) Assay Results:
1) Field DRT Validation Results of OsHDA14 (DP0539) Transgenic Rice Twelve OsHDA14 transgenic lines were tested in Hainan Province in the first experiment. Watering was stopped from panicle initiation stage V-VI of the main stem panicle to seed maturity to produce heavier drought stress. The soil volumetric water content decreased from 39% to 7% during heading and maturation stage. 19 days after stopping watering, the main stem panicles were at panicle initiation stage VIII, the tiller panicles were at panicle initiation stage VI-VII, and some rice plants exhibited phenotypes such as leaf rolling. At the end of the planting season, the transgenic rice plants DP0539.04, DP0539.08, DP0539.09 and DP0539.12 exhibited good seed setting rate.

The grain yield per plant is shown in Table 6, the OsHDA14 transgenic rice plants showed greater grain yield per plant than both ZH11-TC and DP0158 plants at the construct level. Eleven OsHDA14 transgenic rice lines showed greater grain yield per plant than ZH11-TC and DP0158 plants at the line level. These results indicate that OsHDA14 transgenic rice plant had greater grain yield per plant than controls after drought stress.

TABLE 6

Grain yield analysis of OsHDA14 transgenic rice plants under field drought conditions (1$^{st}$ experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0539 (Construct) | 469 | 277 | 7.88 | 1.04 | 0.355 | | 1.05 | 0.347 | |
| ZH11-TC | 40 | 24 | 6.84 | | | | | | |
| DP0158 | 40 | 24 | 6.83 | | | | | | |
| DP0539.01 | 40 | 23 | 8.04 | 1.20 | 0.359 | | 1.21 | 0.352 | |
| DP0539.02 | 40 | 24 | 8.17 | 1.33 | 0.300 | | 1.34 | 0.302 | |
| DP0539.03 | 39 | 24 | 7.84 | 1.00 | 0.443 | | 1.01 | 0.429 | |
| DP0539.04 | 40 | 24 | 8.52 | 1.68 | 0.196 | | 1.70 | 0.190 | |
| DP0539.06 | 39 | 24 | 7.79 | 0.94 | 0.467 | | 0.96 | 0.454 | |
| DP0539.08 | 38 | 23 | 8.73 | 1.89 | 0.146 | | 1.90 | 0.134 | |
| DP0539.09 | 38 | 22 | 8.58 | 1.74 | 0.181 | | 1.75 | 0.178 | |
| DP0539.10 | 40 | 24 | 6.94 | 0.10 | 0.939 | | 0.11 | 0.932 | |
| DP0539.11 | 40 | 24 | 6.54 | −0.30 | 0.824 | | −0.29 | 0.830 | |
| DP0539.12 | 39 | 22 | 9.04 | 2.20 | 0.091 | Y | 2.21 | 0.088 | Y |
| DP0539.13 | 40 | 24 | 7.37 | 0.53 | 0.686 | | 0.54 | 0.678 | |
| DP0539.15 | 36 | 19 | 7.02 | 0.18 | 0.890 | | 0.19 | 0.884 | |

The second experiment was performed in Ningxia province; the same twelve OsHDA14 transgenic lines were tested. When the main stem panicles reached panicle initiation stage I, watering was stopped. The soil volumetric water content decreased from 50% to 10% after stopping watering for 16 days, and the following rainfall made the soil volumetric water content varied during heading stage and maturity stage. 16 days later, the main stem panicles reached panicle imitation stage IV-V, and the rice plants showed leaf rolling phenotype. The transgenic rice plants DP0539.04, DP0539.06 and DP0539.12 exhibited good seed setting rate at the end of planting season.

As shown in Table 7, OsHDA14 transgenic rice exhibited greater grain yield per plant than ZH11-TC control and DP0158 control at the construct level. Eight lines had greater grain yields per plant than ZH11-TC and DP0158 controls. The three transgenic lines which showed good setting rate exhibited significantly greater grain yield per plant than both ZH11-TC and DP0158 controls. These results further demonstrate that OsHDA14 rice plant is tolerance to drought stress, and over-expression of OsHDA14 increases the grain yield per plant after drought stress at flowering and heading stage.

TABLE 7

Grain yield analysis of OsHDA14 transgenic rice plants under field drought conditions (2nd experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0539 (Construct) | 474 | 284 | 5.02 | 0.59 | 0.407 | | 0.90 | 0.210 | |
| ZH11-TC | 40 | 24 | 4.43 | | | | | | |
| DP0158 | 40 | 24 | 4.12 | | | | | | |
| DP0539.01 | 39 | 24 | 4.76 | 0.34 | 0.675 | | 0.65 | 0.430 | |
| DP0539.02 | 38 | 24 | 4.77 | 0.34 | 0.676 | | 0.65 | 0.427 | |
| DP0539.03 | 40 | 24 | 4.85 | 0.43 | 0.601 | | 0.74 | 0.370 | |
| DP0539.04 | 40 | 24 | 5.84 | 1.42 | 0.082 | Y | 1.73 | 0.031 | Y |
| DP0539.06 | 40 | 24 | 6.03 | 1.61 | 0.051 | Y | 1.92 | 0.018 | Y |
| DP0539.08 | 40 | 24 | 5.01 | 0.58 | 0.476 | | 0.90 | 0.282 | |
| DP0539.09 | 40 | 24 | 3.84 | −0.58 | 0.467 | | −0.27 | 0.739 | |
| DP0539.10 | 39 | 22 | 4.29 | −0.14 | 0.867 | | 0.17 | 0.832 | |
| DP0539.11 | 40 | 24 | 4.30 | −0.12 | 0.887 | | 0.19 | 0.828 | |
| DP0539.12 | 40 | 24 | 7.82 | 3.39 | 0.000 | Y | 3.70 | 0.000 | Y |
| DP0539.13 | 39 | 24 | 5.09 | 0.66 | 0.413 | | 0.97 | 0.243 | |
| DP0539.15 | 39 | 22 | 3.58 | −0.84 | 0.291 | | −0.53 | 0.507 | |

2) Field DRT Validation Results of OsZCW7 (DP0924) Transgenic Rice

Twelve OsZCW7 transgenic rice plants were tested in Hainan field. ZH11-TC and DP0158 rice plants planted nearby were used as controls. When the main stem panicles reached panicle initiation stage II-IV, watering was stopped. The soil volumetric water content decreased from 27% to 5% during panicle heading and maturation stage to produce heavier drought stress. 23 days after stopping watering, the main stem panicles headed out, the tiller panicles reached panicle initiation stage VI-VII, and the rice plants began to show leaf roll phenotype. At the maturation stage, three transgenic rice lines DP0924.05, DP0924.07 and DP0924.15 showed better seed setting phenotype.

At the end of the growing season, about six representative plants from each transgenic line were harvested from the middle of the row per line, and grain yield per plant was measured. The grain yield per plant of OsZCW7 transgenic rice was greater than ZH11-TC control and significantly greater than DP0158 control at the construct level. Three OsZCW7 transgenic lines showed significantly greater grain yield per plants than ZH11-TC plants, and ten transgenic lines showed significantly greater grain yield per plants than DP0158 control plants. The three transgenic lines which showed better seed setting rates exhibited significantly greater grain yield per plant than ZH11-TC and DP0158 controls (Table 8). These results indicate that OsZCW7 transgenic rice plant is tolerance to drought conditions, and over-expression of OsZCW7 increased drought tolerance at seedling stage and increase the grain yield per plant after drought stress at flowering stage.

TABLE 8

Grain yield analysis of OsZCW7 transgenic rice plants under field drought conditions (1st experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0924 (Construct) | 422 | 224 | 2.22 | 0.70 | 0.209 | | 1.58 | 0.004 | Y |
| ZH11-TC | 36 | 18 | 1.52 | | | | | | |
| DP0158 | 36 | 18 | 0.64 | | | | | | |
| DP0924.02 | 35 | 18 | 1.93 | 0.41 | 0.526 | | 1.29 | 0.042 | Y |
| DP0924.03 | 36 | 19 | 2.35 | 0.82 | 0.197 | | 1.71 | 0.007 | Y |
| DP0924.04 | 33 | 19 | 1.89 | 0.37 | 0.560 | | 1.26 | 0.047 | Y |
| DP0924.05 | 36 | 18 | 2.65 | 1.13 | 0.078 | Y | 2.01 | 0.002 | Y |
| DP0924.06 | 34 | 18 | 1.58 | 0.06 | 0.929 | | 0.94 | 0.138 | |
| DP0924.07 | 35 | 20 | 2.58 | 1.05 | 0.097 | Y | 1.94 | 0.002 | Y |
| DP0924.08 | 36 | 19 | 2.14 | 0.61 | 0.338 | | 1.50 | 0.019 | Y |
| DP0924.09 | 36 | 19 | 2.30 | 0.78 | 0.224 | | 1.66 | 0.009 | Y |
| DP0924.10 | 34 | 18 | 1.66 | 0.14 | 0.832 | | 1.02 | 0.106 | |
| DP0924.13 | 36 | 18 | 2.10 | 0.58 | 0.359 | | 1.47 | 0.020 | Y |
| DP0924.15 | 36 | 20 | 3.31 | 1.79 | 0.005 | Y | 2.67 | 0.000 | Y |
| DP0924.16 | 35 | 18 | 2.13 | 0.61 | 0.335 | | 1.50 | 0.017 | Y |

The second experiment was performed in Hainan province, the twelve OsZCW7 transgenic lines were tested. When the main stem panicles reached panicle initiation stage V-VI, and the tiller panicles reached panicle initiation stage II-DI, watering was stopped. The soil volumetric water content decreased from 21% to 7% during panicle heading stage. 49 days after stopping watering, the main stem panicles reached milk mature stage, and the rice plants showed leaf rolling phenotype. At the maturation stage, four transgenic rice lines DP0924.03, DP0924.07, DP0924.13 and DP0924.15 showed better seed setting phenotype.

As shown in Table 9, OsZCW7 transgenic rice exhibited significantly greater grain yield per plant than both ZH11-TC and DP0158 controls at the construct level. Nine OsZCW7 transgenic lines had significantly greater grain yields per plant than ZH11-TC and DP0158 controls. Two transgenic lines DP0924.07 and DP0924.15 showed the greatest grain yields per plants in the two experiments. These results further demonstrate that OsZCW7 transgenic rice plant is tolerance to drought, and over-expression of OsZCW7 increases the grain yield per plant after drought stress at flowering and heading stage.

stem panicles reached panicle initiation stage IV-V. The soil volumetric water content decreased from 21% to 5% during heading and maturation stage. 52 days after stopping watering, the main stem panicles were at milk mature stage, the rice plants showed drought stress phenotype such as leaf rolling and leaf yellow. Seven transgenic lines DP0994.02, DP0994.03, DP0994.04, DP0994.09, DP0994.10, DP0994.11, and DP0994.14 exhibited better seed setting phenotypes.

As shown in Table 10, the OsCCS1 transgenic rice plants showed significantly greater grain yield per plant than both ZH11-TC and DP0158 controls at the construct level. Six transgenic lines exhibited significantly greater grain yields per plant than both ZH11-TC and DP0158 controls at the

TABLE 9

Grain yield analysis of OsZCW7 transgenic rice plants under field drought conditions ($2^{nd}$ experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0924 (Construct) | 467 | 282 | 8.00 | 2.93 | 0.003 | Y | 4.13 | 0.000 | Y |
| ZH11-TC | 38 | 24 | 5.08 | | | | | | |
| DP0158 | 40 | 24 | 3.87 | | | | | | |
| DP0924.02 | 40 | 24 | 6.15 | 1.07 | 0.312 | | 2.28 | 0.032 | Y |
| DP0924.03 | 30 | 18 | 6.73 | 1.65 | 0.146 | | 2.85 | 0.012 | Y |
| DP0924.04 | 40 | 24 | 8.86 | 3.78 | 0.000 | Y | 4.98 | 0.000 | Y |
| DP0924.05 | 40 | 24 | 8.61 | 3.53 | 0.001 | Y | 4.74 | 0.000 | Y |
| DP0924.07 | 40 | 24 | 10.34 | 5.26 | 0.000 | Y | 6.47 | 0.000 | Y |
| DP0924.08 | 40 | 24 | 6.57 | 1.49 | 0.161 | | 2.69 | 0.010 | Y |
| DP0924.09 | 40 | 24 | 8.08 | 3.00 | 0.005 | Y | 4.21 | 0.000 | Y |
| DP0924.10 | 40 | 24 | 6.89 | 1.81 | 0.089 | Y | 3.02 | 0.004 | Y |
| DP0924.11 | 40 | 24 | 7.22 | 2.14 | 0.041 | Y | 3.35 | 0.001 | Y |
| DP0924.13 | 40 | 24 | 7.96 | 2.88 | 0.007 | Y | 4.09 | 0.000 | Y |
| DP0924.15 | 40 | 24 | 9.96 | 4.88 | 0.000 | Y | 6.09 | 0.000 | Y |
| DP0924.16 | 37 | 24 | 8.68 | 3.60 | 0.001 | Y | 4.80 | 0.000 | Y |

3) Field DRT Validation Results of OsCCS1 (DP0994) Transgenic Rice

Twelve OsCCS1 transgenic lines were tested in Hainan in the first experiment. Watering was stopped when the main line level. These results demonstrate that OsCCS1 transgenic rice plant is tolerant to drought stress and over-expression of OsCCS1 increased the grain yield per plant after drought stress at flowering stage.

TABLE 10

Grain yield analysis of OsCCS1 transgenic rice plants under field drought conditions ($1^{st}$ experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0994 (Construct) | 470 | 278 | 7.20 | 2.16 | 0.023 | Y | 3.98 | 0.000 | Y |
| ZH11-TC | 40 | 24 | 5.04 | | | | | | |
| DP0158 | 40 | 24 | 3.22 | | | | | | |
| DP0994.02 | 40 | 24 | 7.56 | 2.52 | 0.012 | Y | 4.34 | 0.000 | Y |
| DP0994.03 | 40 | 24 | 11.44 | 6.40 | 0.000 | Y | 8.22 | 0.000 | Y |
| DP0994.04 | 40 | 24 | 8.41 | 3.38 | 0.001 | Y | 5.19 | 0.000 | Y |
| DP0994.06 | 40 | 24 | 3.96 | −1.08 | 0.285 | | 0.74 | 0.464 | |
| DP0994.07 | 40 | 24 | 6.25 | 1.22 | 0.229 | | 3.03 | 0.003 | Y |
| DP0994.08 | 40 | 20 | 2.70 | −2.34 | 0.020 | | −0.52 | 0.602 | |
| DP0994.09 | 40 | 24 | 8.73 | 3.70 | 0.000 | Y | 5.52 | 0.000 | Y |
| DP0994.10 | 40 | 24 | 5.71 | 0.67 | 0.496 | | 2.49 | 0.013 | Y |
| DP0994.11 | 40 | 24 | 11.17 | 6.14 | 0.000 | Y | 7.96 | 0.000 | Y |
| DP0994.12 | 40 | 24 | 6.49 | 1.45 | 0.151 | | 3.27 | 0.001 | Y |
| DP0994.13 | 30 | 18 | 4.87 | −0.17 | 0.875 | | 1.65 | 0.121 | |
| DP0994.14 | 40 | 24 | 9.09 | 4.06 | 0.000 | Y | 5.88 | 0.000 | Y |

The second experiment was performed in Ningxia province; the same twelve OsCCS1 transgenic lines were tested. Watering was stopped when the main stem panicles reached to panicle initiation stage I. The soil volumetric water content decreased from 60% to 20% after stopping watering for 26 days. The main stem panicles reached panicle initiation stage VII-VIII, and the rice plants started to show leaf rolling phenotype. 35 days after stopping watering, the panicles headed out. Many transgenic rice lines showed better seed setting phenotype.

The OsCCS1 transgenic rice plants showed greater grain yield per plant than DP0158 control at the construct level. Analysis at line level showed that five OsCCS1 transgenic lines showed significantly greater grain yield per plant than the DP0158 control plants (Table 11). These results further demonstrate that OsCCS1 over-expressed transgenic rice plant is tolerance to drought stress, and over-expression of OsCCS1 increased the drought tolerance and then increased the grain yield per plant.

TABLE 11

Grain yield analysis of OsCCS1 transgenic rice plants under field drought conditions ($2^{nd}$ experiment)

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0994 (Construct) | 465 | 285 | 7.78 | −0.48 | 0.723 | | 1.03 | 0.453 | |
| ZH11-TC | 40 | 24 | 8.26 | | | | | | |
| DP0158 | 40 | 24 | 6.75 | | | | | | |
| DP0994.02 | 40 | 24 | 9.75 | 1.50 | 0.358 | | 3.01 | 0.068 | Y |
| DP0994.03 | 39 | 24 | 9.81 | 1.55 | 0.337 | | 3.06 | 0.062 | Y |
| DP0994.04 | 38 | 24 | 9.69 | 1.43 | 0.389 | | 2.94 | 0.079 | Y |
| DP0994.06 | 40 | 24 | 5.50 | −2.75 | 0.094 | | −1.24 | 0.454 | |
| DP0994.07 | 40 | 24 | 4.76 | −3.50 | 0.030 | | −1.99 | 0.224 | |
| DP0994.08 | 38 | 22 | 6.51 | −1.75 | 0.249 | | −0.24 | 0.880 | |
| DP0994.09 | 40 | 24 | 9.09 | 0.83 | 0.607 | | 2.34 | 0.154 | |
| DP0994.10 | 40 | 24 | 6.62 | −1.64 | 0.308 | | −0.13 | 0.936 | |
| DP0994.11 | 40 | 24 | 9.49 | 1.23 | 0.405 | | 2.74 | 0.054 | Y |
| DP0994.12 | 40 | 24 | 9.80 | 1.55 | 0.295 | | 3.06 | 0.033 | Y |
| DP0994.13 | 36 | 24 | 6.05 | −2.21 | 0.123 | | −0.70 | 0.653 | |
| DP0994.14 | 34 | 23 | 6.25 | −2.01 | 0.197 | | −0.50 | 0.733 | |

4) Field DRT Validation Results of OsDN-DTP10 (DP0999) Transgenic Rice

Twelve OsDN-DTP10 transgenic rice plants were tested in Hainan field. ZH11-TC and DP0158 rice plants were used as controls. When the main stem panicles reached panicle initiation stage III-V, watering was stopped. The soil volumetric water content decreased from 24% to 7% during panicle heading and maturation stage. 52 days after stopping watering, the main stem panicles reached milk mature stage, and the rice plants started to show drought stress phenotype. Three lines DP0999.03, DP0999.10 and DP0999.11 showed better seed setting at the maturation stage.

At the end of the growing season, the grain yield per plant was measured. The grain yield per plant of OsDN-DTP10 transgenic rice was greater than both ZH11-TC and DP0158 control at the construct level. Six OsDN-DTP10 transgenic lines showed significantly greater grain yield per plants than ZH11-TC plants, and seven transgenic lines showed significantly greater grain yield per plants than DP0158 control plants (Table 12). These results indicate that OsDN-DTP10 transgenic rice plant is tolerance to drought conditions, and over-expression of OsDN-DTP10 increased drought tolerance at seedling stage and increased the grain yield per plant after drought stress at flowering stage.

TABLE 12

Grain yield analysis of OsDN-DTP10 transgenic rice plants under field drought conditions (1st experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0999 (Construct) | 478 | 288 | 7.26 | 1.49 | 0.130 | | 2.52 | 0.011 | Y |
| ZH11-TC | 40 | 24 | 5.77 | | | | | | |
| DP0158 | 40 | 24 | 4.74 | | | | | | |
| DP0999.01 | 40 | 24 | 6.41 | 0.64 | 0.550 | | 1.67 | 0.122 | |
| DP0999.03 | 40 | 24 | 8.60 | 2.83 | 0.009 | Y | 3.86 | 0.000 | Y |
| DP0999.04 | 40 | 24 | 6.70 | 0.92 | 0.393 | | 1.95 | 0.071 | Y |
| DP0999.05 | 40 | 24 | 6.25 | 0.47 | 0.661 | | 1.51 | 0.165 | |
| DP0999.07 | 40 | 24 | 5.83 | 0.06 | 0.959 | | 1.09 | 0.320 | |
| DP0999.09 | 39 | 24 | 8.14 | 2.37 | 0.030 | Y | 3.40 | 0.002 | Y |
| DP0999.10 | 40 | 24 | 7.74 | 1.97 | 0.071 | Y | 3.00 | 0.006 | Y |
| DP0999.11 | 40 | 24 | 9.52 | 3.75 | 0.001 | Y | 4.78 | 0.000 | Y |
| DP0999.12 | 40 | 24 | 5.92 | 0.15 | 0.890 | | 1.18 | 0.276 | |
| DP0999.13 | 40 | 24 | 6.43 | 0.65 | 0.546 | | 1.68 | 0.124 | |
| DP0999.14 | 39 | 24 | 7.86 | 2.09 | 0.051 | Y | 3.12 | 0.003 | Y |
| DP0999.15 | 40 | 24 | 7.76 | 1.99 | 0.061 | Y | 3.02 | 0.005 | Y |

The same 12 OsDN-DTP10 transgenic rice plants were tested again in Ningxia field. Watering was stopped when the main stem panicles reached panicle initiation stage I 27 days after stopping watering, the main stem panicles reached panicle initiation stage VII-VIII, and the rice plants started to show drought stress phenotype. The soil volumetric water content decreased from 50% to 20% during heading stage. Six transgenic lines DP0999.01, DP0999.05, DP0999.09, DP0999.12, DP0999.13 and DP0999.14 showed good seed setting phenotype at mature stage.

Grain yield analysis showed that OsDN-DTP10 transgenic rice plants exhibited greater grain yield per plant than ZH11-TC and DP0158 controls at the construct level. Eleven OsDN-DTP10 transgenic lines exhibited greater grain yield per plant than ZH11-TC and DP0158 control at the line level (Table 13). These results further indicate that OsDN-DTP10 transgenic rice plant gained drought tolerance and exhibited grain yield increase per plant.

5) Field DRT Validation Results of OsDN-DTP11 (DP1131) Transgenic Rice

Twelve OsDN-DTP11 transgenic rice plants were tested in Hainan field. ZH11-TC and DP0158 rice plants planted were used as controls. When the main stem panicles reached panicle initiation stage II-III, watering was stopped. The soil volumetric water content decreased from 40% to 10% during panicle heading and maturation stage. 19 days after stopping watering, the main stem panicles reached panicle initiation stage VIII, the tiller panicles reached panicle initiation stage V-VI, and the rice plants began to show leaf roll phenotype. The OsDN-DTP11 transgenic lines showed less leaf rolling degree and less drying leaf than control plants during the drought stress. Three transgenic lines DP1131.01, DP1131.03 and DP1131.06 showed better seed setting at the maturation stage.

The grain yield analysis showed that the grain yield per plant of OsDN-DTP11 transgenic rice was greater than ZH11-TC and significantly greater than DP0158 control at

TABLE 13

Grain yield analysis of OsDN-DTP10 transgenic rice plants under field drought conditions (2nd experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0999 (Construct) | 475 | 288 | 4.90 | 0.95 | 0.310 | | 2.30 | 0.016 | Y |
| ZH11-TC | 40 | 24 | 3.95 | | | | | | |
| DP0158 | 37 | 18 | 2.60 | | | | | | |
| DP0999.01 | 40 | 24 | 5.10 | 1.15 | 0.297 | | 2.49 | 0.025 | Y |
| DP0999.03 | 40 | 24 | 4.45 | 0.50 | 0.642 | | 1.84 | 0.095 | Y |
| DP0999.04 | 40 | 24 | 4.52 | 0.57 | 0.600 | | 1.92 | 0.076 | Y |
| DP0999.05 | 40 | 24 | 5.39 | 1.44 | 0.193 | | 2.79 | 0.015 | Y |
| DP0999.07 | 40 | 24 | 5.79 | 1.84 | 0.093 | Y | 3.19 | 0.004 | Y |
| DP0999.09 | 39 | 24 | 5.56 | 1.61 | 0.143 | | 2.96 | 0.008 | Y |
| DP0999.10 | 39 | 24 | 4.41 | 0.47 | 0.663 | | 1.81 | 0.102 | |
| DP0999.11 | 40 | 24 | 4.08 | 0.13 | 0.909 | | 1.48 | 0.198 | |
| DP0999.12 | 40 | 24 | 5.68 | 1.73 | 0.115 | | 3.08 | 0.006 | Y |
| DP0999.13 | 39 | 24 | 3.89 | −0.06 | 0.957 | | 1.29 | 0.229 | |
| DP0999.14 | 39 | 24 | 5.39 | 1.45 | 0.202 | | 2.79 | 0.012 | Y |
| DP0999.15 | 39 | 24 | 4.55 | 0.60 | 0.585 | | 1.95 | 0.080 | Y | the construct level. Five OsDN-DTP11 transgenic lines showed significantly greater grain yields per plants than ZH11-TC plants, and seven OsDN-DTP11 transgenic lines showed significantly greater grain yields per plants than DP0158 control plants (Table 14). These results indicate that OsDN-DTP11 transgenic rice plant is tolerance to drought conditions, and over-expression of OsDN-DTP11 increased drought tolerance at seedling stage and increased the grain yield per plant after drought stress at flowering stage.

drought stress phenotype. The soil volumetric water content decreased from 17% to 6% during heading stage. Six transgenic rice lines DP1131.01, DP1131.02, DP1131.03, DP1131.04, DP1131.08 and DP1131.10 were recorded to show better seed setting phenotype.

Grain yield analysis showed that OsDN-DTP11 transgenic rice plants exhibited significantly greater grain yield per plant than ZH11-TC and DP0158 controls at the con-

TABLE 14

Grain yield analysis of OsDN-DTP11 transgenic rice plants under field drought conditions (1$^{st}$ experiment)

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP1131 (Construct) | 422 | 264 | 6.87 | 0.46 | 0.605 | | 2.37 | 0.008 | Y |
| ZH11-TC | 40 | 23 | 6.41 | | | | | | |
| DP0158 | 40 | 24 | 4.50 | | | | | | |
| DP1131.01 | 40 | 26 | 9.29 | 2.89 | 0.003 | Y | 4.79 | 0.000 | Y |
| DP1131.02 | 37 | 24 | 8.25 | 1.84 | 0.060 | Y | 3.74 | 0.000 | Y |
| DP1131.03 | 40 | 23 | 9.05 | 2.64 | 0.007 | Y | 4.55 | 0.000 | Y |
| DP1131.04 | 38 | 23 | 6.53 | 0.12 | 0.897 | | 2.03 | 0.034 | Y |
| DP1131.06 | 38 | 24 | 8.91 | 2.50 | 0.008 | Y | 4.41 | 0.000 | Y |
| DP1131.07 | 30 | 18 | 3.53 | −2.88 | 0.005 | | −0.97 | 0.349 | |
| DP1131.08 | 30 | 18 | 8.01 | 1.60 | 0.122 | | 3.51 | 0.001 | Y |
| DP1131.09 | 35 | 23 | 8.48 | 2.07 | 0.033 | Y | 3.97 | 0.000 | Y |
| DP1131.10 | 35 | 24 | 6.03 | −0.38 | 0.698 | | 1.53 | 0.117 | |
| DP1131.11 | 29 | 18 | 4.19 | −2.22 | 0.032 | | −0.31 | 0.762 | |
| DP1131.13 | 30 | 18 | 4.56 | −1.85 | 0.072 | | 0.05 | 0.959 | |
| DP1131.14 | 40 | 25 | 5.61 | −0.80 | 0.382 | | 1.10 | 0.256 | |

The same 12 OsDN-DTP11 transgenic rice plants were tested again in Hainan field. Watering was stopped when the main stem panicles reached panicle initiation stage IV-V and the tiller panicles reached panicle initiation stage II-III. 49 days after stopping watering, the main stem panicles reached milk mature stage, and the rice plants started to show struct level. All the OsDN-DTP11 transgenic lines exhibited greater grain yields per plant than ZH11-TC and DP0158 controls at the line level (Table 15). These results further indicate that OsDN-DTP11 transgenic rice plant gained drought tolerance and exhibited greater grain yield increase per plant.

TABLE 15

Grain yield analysis of OsDN-DTP11 transgenic rice plants under field drought conditions (2$^{nd}$ experiment)

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP1131 (Construct) | 480 | 288 | 6.44 | 3.03 | 0.005 | Y | 2.78 | 0.011 | Y |
| ZH11-TC | 40 | 24 | 3.41 | | | | | | |
| DP0158 | 40 | 24 | 3.66 | | | | | | |
| DP1131.01 | 40 | 24 | 9.87 | 6.46 | 0.000 | Y | 6.21 | 0.000 | Y |
| DP1131.02 | 40 | 24 | 9.23 | 5.81 | 0.000 | Y | 5.57 | 0.000 | Y |
| DP1131.03 | 40 | 24 | 9.14 | 5.73 | 0.000 | Y | 5.48 | 0.000 | Y |
| DP1131.04 | 40 | 24 | 4.02 | 0.61 | 0.607 | | 0.36 | 0.759 | |
| DP1131.06 | 40 | 24 | 8.03 | 4.62 | 0.000 | Y | 4.37 | 0.000 | Y |
| DP1131.07 | 40 | 24 | 3.68 | 0.27 | 0.821 | | 0.02 | 0.985 | |
| DP1131.08 | 40 | 24 | 7.14 | 3.73 | 0.002 | Y | 3.48 | 0.003 | Y |
| DP1131.09 | 40 | 24 | 6.07 | 2.66 | 0.023 | Y | 2.42 | 0.040 | Y |
| DP1131.10 | 40 | 24 | 6.21 | 2.80 | 0.017 | Y | 2.55 | 0.029 | Y |
| DP1131.11 | 40 | 24 | 4.02 | 0.61 | 0.601 | | 0.37 | 0.754 | |
| DP1131.13 | 40 | 24 | 3.68 | 0.27 | 0.817 | | 0.02 | 0.987 | |
| DP1131.14 | 40 | 24 | 6.17 | 2.76 | 0.017 | Y | 2.51 | 0.032 | Y |

Example 6

Laboratory Paraquat Assays of Transgenic Rice Plants

Paraquat (1,1-dimethyl-4,4-bipyridinium dichloride), is a foliar-applied and non-selective bipyridinium herbicide, and it is one of the most widely used herbicides in the world, controlling weeds in a huge variety of crops like corn, rice, soybean etc. In plant cells, paraquat mainly targets chloroplasts by accepting electrons from photosystem I and then reacting with oxygen to produce superoxide and hydrogen peroxide, which cause photooxidative stress. Drought stress usually leads to increased reactive oxygen species (ROS) in plants and sometimes, the drought tolerance of plant is associated with enhanced antioxidative ability. Paraquat is a potent oxidative stress inducer; it greatly increases the ROS production and inhibits the regeneration of reducing equivalents and compounds necessary for the activity of the antioxidant system. The ROS generation is enhanced under abiotic stress conditions, and the plant responses range from tolerance to death depending on the stress intensity and its associated-ROS levels. Relative low level of paraquat can mimic the stress-associated ROS production and used as a stress tolerance marker in plant stress biology (Hasaneen M. N. A. (2012) Herbicide-Properties, Synthesis and Control of Weeds book). Therefore, the paraquat tolerance of the drought tolerant transgenic rice plants was tested.

Paraquat Assay Methods:

Transgenic rice plants from ten transgenic lines were tested by paraquat assay. Tissue-cultured Zhonghua 11 plants (ZH11-TC) and empty vector transgenic plants (DP0158) were used as controls. T2 transgenic seeds were sterilized and germinated, and this assay was carried out in growth room with temperature at 28~30° C. and humidity ~30%. The germinated seeds were placed in a tube with a hole at the bottom, and water cultured at 30° C. for 5 days till one-leaf and one-terminal bud stage. Uniform seedlings about 3.5~4 cm in height were selected for paraquat testing. Randomized block design was used in this experiment. There were five blocks, each of which has 16×12 holes. Each transgenic line was placed in one row (12 plants/line), and ZH11-TC and DP0158 seedlings were placed in 3 rows (3×12 plants) randomly in one block. Then the seedlings were treated with 0.8 µM paraquat solution for 7 days at 10 h day/14 h night, and the treated seedlings first encountered dark and took up the paraquat solution which was changed every two days. After treated for 7 days, the green seedlings were counted. Those seedlings that maintain green in whole without damage were considered as paraquat tolerant seedling; those with bleached leaves or stem were not considered as paraquat tolerant seedling.

Tolerance rate was used as a parameter for this trait screen, which is the percentage of plants which kept green and showed tolerant phenotype over the total plant number.

The data was analyzed at construct level (all transgenic plants compared with the control) and transgenic line level (different transgenic lines compared with the control) using a statistic model of "Y~seg+line (seg)+rep+error", random effect of "rep", Statistic Method of "SAS® PROC GLIMMIX".

Paraquat Assay Results:

1) Paraquat Validation Results of OsHDA14 (DP0539) Transgenic Rice

In the first experiment, after paraquat solution treated for seven days, 350 of the 600 OsHDA14 transgenic seedlings (58%) kept green and showed tolerant phenotype, while 39 of the 180 (22%) seedlings from ZH11-TC showed tolerant phenotype, and 63 of the 180 (35%) DP0158 seedlings showed tolerant phenotype. The tolerance rate of all screened OsHDA14 transgenic seedlings was significantly greater than ZH11-TC and DP0158 controls at the construct level.

Further analysis at transgenic line level indicates that nine OsHDA14 transgenic lines had significantly greater tolerance rates than ZH11-TC control and eight lines had significantly greater tolerance rates than DP0158 control (Table 16). These results demonstrate that OsHDA14 transgenic rice plants had enhanced paraquat tolerance compared to both controls of ZH11-TC and DP0158 rice plants at construct and transgenic line level at seedling stages. OsHDA14 functions in enhancing paraquat tolerance or antioxidative ability of transgenic plants.

TABLE 16

Paraquat tolerance assay of OsHDA14 transgenic rice plants (1$^{st}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0539 (Construct) | 350 | 600 | 58 | 0.0000 | Y | 0.0000 | Y |
| ZH11-TC | 39 | 180 | 22 | | | | |
| DP0158 | 63 | 180 | 35 | | | | |
| DP0539.01 | 36 | 60 | 60 | 0.0000 | Y | 0.0014 | Y |
| DP0539.02 | 42 | 60 | 70 | 0.0000 | Y | 0.0000 | Y |
| DP0539.03 | 41 | 60 | 68 | 0.0000 | Y | 0.0000 | Y |
| DP0539.04 | 37 | 60 | 62 | 0.0000 | Y | 0.0007 | Y |
| DP0539.06 | 48 | 60 | 80 | 0.0000 | Y | 0.0000 | Y |
| DP0539.09 | 18 | 60 | 30 | 0.1954 | | 0.4807 | |
| DP0539.10 | 26 | 60 | 43 | 0.0021 | Y | 0.2523 | |
| DP0539.12 | 34 | 60 | 57 | 0.0000 | Y | 0.0048 | Y |
| DP0539.13 | 30 | 60 | 50 | 0.0001 | Y | 0.0443 | Y |
| DP0539.15 | 38 | 60 | 63 | 0.0000 | Y | 0.0004 | Y |

In the second experiment, ten same OsHDA14 transgenic lines were tested. Seven days later, 472 of the 600 OsHDA14 transgenic seedlings (79%) kept green and showed tolerant phenotype, while 125 of the 180 (69%) seedlings from ZH11-TC showed tolerant phenotype, and 122 of the 180 (68%) DP0158 seedlings showed tolerant phenotype. The tolerance rate of all screened OsHDA14 transgenic seedlings was significantly greater than ZH11-TC and DP0158 controls at the construct level.

Further analysis at transgenic line level indicates that three OsHDA14 transgenic lines had significantly greater tolerance rates than both ZH11-TC control and DP0158 control (Table 17). These results further demonstrate that OsHDA14 functions in enhancing paraquat tolerance or antioxidative ability of transgenic plants.

Further analysis at transgenic line level is displayed in Table 19. Four OsCCS1 transgenic lines had significantly higher tolerance rates than ZH11-TC control. These results show that over-expression OsCCS1 gene increased the paraquat tolerance. OsCCS1 plays a role in enhancing paraquat tolerance or antioxidative ability of the transgenic plants.

TABLE 17

Paraquat tolerance assay of OsHDA14 transgenic rice plants (2$^{nd}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0539 (Construct) | 472 | 600 | 79 | 0.0064 | Y | 0.0018 | Y |
| ZH11-TC | 125 | 180 | 69 | | | | |
| DP0158 | 122 | 180 | 68 | | | | |
| DP0539.01 | 43 | 60 | 72 | 0.7458 | | 0.5749 | |
| DP0539.02 | 46 | 60 | 77 | 0.2891 | | 0.1989 | |
| DP0539.03 | 41 | 60 | 68 | 0.8714 | | 0.9367 | |
| DP0539.04 | 46 | 60 | 77 | 0.2891 | | 0.1989 | |
| DP0539.06 | 45 | 60 | 75 | 0.4153 | | 0.2965 | |
| DP0539.09 | 47 | 60 | 78 | 0.1919 | | 0.1276 | |
| DP0539.10 | 52 | 60 | 87 | 0.0132 | Y | 0.0079 | Y |
| DP0539.12 | 45 | 60 | 75 | 0.4153 | | 0.2965 | |
| DP0539.13 | 54 | 60 | 90 | 0.0039 | Y | 0.0023 | Y |
| DP0539.15 | 53 | 60 | 88 | 0.0072 | Y | 0.0043 | Y |

2) Paraquat Validation Results of OsCCS1 (DP0994) Transgenic Rice

In the first experiment, 436 of the 600 transgenic seedlings (73%) kept green and showed tolerant phenotype after treated with 0.8 μM paraquat solutions for 7 days, while 109 of the 180 (61%) seedlings from ZH11-TC showed tolerant phenotype. The tolerance rate of OsCCS1 transgenic seedlings was significantly higher than ZH11-TC control.

Analysis at transgenic line level is displayed in Table 18. Five OsCCS1 transgenic lines had significantly higher tolerance rates than ZH11-TC control. These results show that over-expression OsCCS1 gene increased the paraquat tolerance or antioxidative ability of the transgenic plants.

TABLE 18

Paraquat tolerance assay of OsCCS1 transgenic rice plants (1$^{st}$ experiment)

| Line ID | Number of tolerant seedlings | Number of total seedlings | Tolerance rate (%) | CK = ZH11-TC P value | P ≤ 0.05 |
|---|---|---|---|---|---|
| DP0994 (Construct) | 436 | 600 | 73 | 0.0013 | Y |
| ZH11-TC | 109 | 180 | 61 | | |
| DP0994.02 | 36 | 60 | 60 | 0.9395 | |
| DP0994.03 | 44 | 60 | 73 | 0.0815 | |
| DP0994.04 | 37 | 60 | 62 | 0.8791 | |
| DP0994.08 | 45 | 60 | 75 | 0.0497 | Y |
| DP0994.09 | 52 | 60 | 87 | 0.0008 | Y |
| DP0994.10 | 45 | 60 | 75 | 0.0497 | Y |
| DP0994.11 | 43 | 60 | 72 | 0.1289 | |
| DP0994.12 | 47 | 60 | 78 | 0.0167 | Y |
| DP0994.13 | 52 | 60 | 87 | 0.0008 | Y |
| DP0994.14 | 35 | 60 | 58 | 0.7619 | |

In the second experiment, the same ten OsCCS1 transgenic lines were tested. 428 of the 600 transgenic seedlings (71%) kept green and showed tolerant phenotype after treated with 0.8 μM paraquat solutions for 7 days, while 104 of the 180 (58%) seedlings from ZH11-TC showed tolerant phenotype. The tolerance rate of OsCCS1 transgenic seedlings was significantly higher than ZH11-TC control.

TABLE 19

Paraquat tolerance assay of OsCCS1 transgenic rice plants (2$^{nd}$ experiment)

| Line ID | Number of tolerant seedlings | Number of total seedlings | Tolerance rate (%) | CK = ZH11-TC P value | P ≤ 0.05 |
|---|---|---|---|---|---|
| DP0994 (Construct) | 428 | 600 | 71 | 0.0006 | Y |
| ZH11-TC | 104 | 180 | 58 | | |
| DP0994.02 | 46 | 60 | 77 | 0.0124 | Y |
| DP0994.03 | 39 | 60 | 65 | 0.3278 | |
| DP0994.04 | 38 | 60 | 63 | 0.4512 | |
| DP0994.08 | 41 | 60 | 68 | 0.1539 | |
| DP0994.09 | 39 | 60 | 65 | 0.3278 | |
| DP0994.10 | 49 | 60 | 82 | 0.0020 | Y |
| DP0994.11 | 52 | 60 | 87 | 0.0003 | Y |
| DP0994.12 | 36 | 60 | 60 | 0.7632 | |
| DP0994.13 | 48 | 60 | 80 | 0.0037 | Y |
| DP0994.14 | 40 | 60 | 67 | 0.2288 | |

3) Paraquat Validation Results of OsDN-DTP10 (DP0999) Transgenic Rice

In the first experiment, 437 of the 600 OsDN-DTP10 transgenic seedlings (73%) kept green and showed tolerant phenotype after treated with paraquat solution, whereas only 115 of the 180 (64%) ZH11-TC seedlings, and 113 of the 180 (63%) DP0158 seedlings showed tolerant phenotype. The tolerance rate of OsDN-DTP10 transgenic plants was significantly higher than that of the ZH11-TC control and DP0158 control at the construct level.

The analysis at transgenic line level is displayed in Table 20. Three lines had significantly greater tolerance rates than either ZH11-TC or DP0158 seedlings, which further demonstrates that OsDN-DTP10 transgenic rice plants had enhanced paraquat tolerance at construct and transgenic line level at seedling stages. Over-expression of OsDN-DTP10 gene improved the paraquat tolerance of the transgenic plants.

TABLE 20

Paraquat tolerance assay of OsDN-DTP10 transgenic rice plants (1st experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0999 (Construct) | 437 | 600 | 73 | 0.0121 | Y | 0.0058 | Y |
| ZH11-TC | 115 | 180 | 64 | | | | |
| DP0158 | 113 | 180 | 63 | | | | |
| DP0999.01 | 35 | 60 | 58 | 0.4447 | | 0.5421 | |
| DP0999.04 | 41 | 60 | 68 | 0.5345 | | 0.4405 | |
| DP0999.05 | 37 | 60 | 62 | 0.7581 | | 0.8781 | |
| DP0999.09 | 48 | 60 | 80 | 0.0261 | Y | 0.0186 | Y |
| DP0999.10 | 43 | 60 | 72 | 0.2767 | | 0.2174 | |
| DP0999.11 | 48 | 60 | 80 | 0.0261 | Y | 0.0186 | Y |
| DP0999.12 | 45 | 60 | 75 | 0.1211 | | 0.0910 | |
| DP0999.13 | 43 | 60 | 72 | 0.2767 | | 0.2174 | |
| DP0999.14 | 43 | 60 | 72 | 0.2767 | | 0.2174 | |
| DP0999.15 | 54 | 60 | 90 | 0.0007 | Y | 0.0005 | Y |

In the second experiment, 376 of the 600 OsDN-DTP10 transgenic seedlings (63%) kept green and showed tolerant phenotype after treated with paraquat solution, whereas only 106 of the 180 (59%) ZH11-TC seedlings, and 103 of the 180 (57%) DP0158 seedlings showed tolerant phenotype. The tolerance rate of OsDN-DTP10 transgenic plants was higher than that of the ZH11-TC control and DP0158 control at the construct level.

The analysis at transgenic line level is displayed in Table 21. Seven lines had greater tolerance rates than either ZH11-TC or DP0158 seedlings, these results further demonstrates that OsDN-DTP10 transgenic rice plants had enhanced paraquat tolerance at construct and transgenic line level at seedling stages. Over-expression of OsDN-DTP10 gene improved the paraquat tolerance of the transgenic plants.

TABLE 21

Paraquat tolerance assay of OsDN-DTP10 transgenic rice plants (2nd experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0999 (Construct) | 376 | 600 | 63 | 0.3400 | | 0.1784 | |
| ZH11-TC | 106 | 180 | 59 | | | | |
| DP0158 | 103 | 180 | 57 | | | | |
| DP0999.01 | 38 | 60 | 63 | 0.5452 | | 0.4087 | |
| DP0999.04 | 36 | 60 | 60 | 0.8800 | | 0.7072 | |
| DP0999.05 | 40 | 60 | 67 | 0.2902 | | 0.2028 | |
| DP0999.09 | 38 | 60 | 63 | 0.5452 | | 0.4087 | |
| DP0999.10 | 35 | 60 | 58 | 0.9399 | | 0.8806 | |
| DP0999.11 | 40 | 60 | 67 | 0.2902 | | 0.2028 | |
| DP0999.12 | 30 | 60 | 50 | 0.2344 | | 0.3341 | |
| DP0999.13 | 43 | 60 | 72 | 0.0841 | | 0.0534 | |
| DP0999.14 | 34 | 60 | 57 | 0.7634 | | 0.9402 | |
| DP0999.15 | 42 | 60 | 70 | 0.1321 | | 0.0864 | |

Example 7

Transformation and Evaluation of Maize with Rice Drought Tolerance Genes

Maize plants can be transformed to over-express *Oryza sativa* drought tolerance genes or a corresponding homolog from maize, *Arabidopsis*, or other species. Expression of the gene in the maize transformation vector can be under control of a constitutive promoter such as the maize ubiquitin promoter (Christensen et al. (1989) *Plant Mol. Biol.* 12:619-632 and Christensen et al. (1992) *Plant Mol. Biol.* 18:675-689) or under control of another promoter, such as a stress-responsive promoter or a tissue-preferred promoter. The recombinant DNA construct can be introduced into maize cells by particle bombardment substantially as described in International Patent Publication WO 2009/006276. Alternatively, maize plants can be transformed with the recombinant DNA construct by *Agrobacterium*-mediated transformation substantially as described by Zhao et al. in *Meth. Mol. Biol.* 318:315-323 (2006) and in Zhao et al., *Mol. Breed.* 8:323-333 (2001) and U.S. Pat. No. 5,981,840 issued Nov. 9, 1999. The *Agrobacterium*-mediated transformation process involves bacterium inoculation, co-cultivation, resting, selection and plant regeneration.

Progeny of the regenerated plants, such as T1 plants, can be subjected to a soil-based drought stress. Using image analysis, plant area, volume, growth rate and color can be measured at multiple times before and during drought stress. Significant delay in wilting or leaf area reduction, a reduced yellow-color accumulation, and/or an increased growth rate during drought stress, relative to a control, will be considered evidence that the gene functions in maize to enhance drought tolerance.

What is claimed is:

1. A plant or seed comprising in its genome a recombinant DNA construct comprising a polynucleotide encoding a polypeptide comprising an amino acid sequence that is at least 95% identical to SEQ ID NO: 6, wherein the plant exhibits improved drought tolerance when compared to a control plant.

2. The plant of claim 1, wherein said plant is selected from the group consisting of rice, maize, soybean, sunflower, sorghum, canola, wheat, alfalfa, cotton, barley, millet, sugar cane and switchgrass.

3. A method of increasing drought tolerance in a plant, the method comprising:
   (a) expressing in a plant a polynucleotide encoding a polypeptide comprising an amino acid sequence of at least 95% identity to SEQ ID NOs: 6 operably linked to a heterologous regulatory element, wherein the expression level of the polynucleotide is increased compared to that of a control plant; and
   (b) selecting a plant of part (a) comprising the polynucleotide operably linked to the regulatory element for increased drought tolerance as compared to a control plant not comprising the polynucleotide operably linked to the regulatory element.

4. The method of claim 3, wherein the expression of the polynucleotide is increased by expressing in the plant a recombinant DNA construct comprising the polynucleotide sequence operably linked to the regulatory element.

5. A method of enhancing grain yield in a rice plant, the method comprising:
   (a) expressing in a plant a polynucleotide encoding a polypeptide comprising an amino acid sequence of at least 95% sequence identity to SEQ ID NOs: 6 operably linked to a heterologous regulatory element, wherein the expression level of the polynucleotide is increased compared to that of a control plant; and
   (b) selecting a plant of part (a) comprising the polynucleotide operably linked to the regulatory element for increased yield as compared to a control plant not comprising the polynucleotide operably linked to the regulatory element.

6. The method of claim 5, wherein the expression of the polynucleotide is increased by expressing in the plant a recombinant DNA construct comprising the polynucleotide sequence operably linked to the regulatory element.

7. The method of claim 3, wherein the heterologous regulatory element is a heterologous promoter.

8. The method of claim 5, wherein the heterologous regulatory element is a heterologous promoter.

9. The method of claim 3, wherein said plant is selected from the group consisting of rice, maize, soybean, sunflower, sorghum, canola, wheat, alfalfa, cotton, barley, millet, sugar cane and switchgrass.

10. The method of claim 5, wherein said plant is selected from the group consisting of rice, maize, soybean, sunflower, sorghum, canola, wheat, alfalfa, cotton, barley, millet, sugar cane and switchgrass.

11. The plant or seed of claim 1, wherein the polynucleotide encodes a polypeptide comprising an amino acid sequence that is at least 99% identical to SEQ ID NO: 6.

12. The plant or seed of claim 11, wherein the plant is selected from the group consisting of rice, maize, or soybean.

* * * * *

SEQUENCE LISTING

<160> NUMBER OF SEQ ID NOS: 35

<210> SEQ ID NO 1
<211> LENGTH: 1480
<212> TYPE: DNA
<213> ORGANISM: Oryza sativa

<400> SEQUENCE: 1

| | | | | | |
|---|---|---|---|---|---|
| gagagataga | tccctggagg | tttgcaggag | gggatggaac | agctgtgggt | gccatcgctt | 60 |
| ccgattcttg | gaggaaggat | attgcctatg | ctcaggcact | actgtggctt | tggaagtcat | 120 |
| catcccttaa | cctggagaag | cttacaaatt | actggaagaa | aacagaagca | taatgggtgt | 180 |
| tggattgcat | actgcttacc | aagccataat | ggaacttcta | tttcagacac | aaatggtgtt | 240 |
| cgaaaagact | tagctttgcc | tgacaatttg | cttcgtgatg | ctcatattct | ctattgtaca | 300 |
| tctcctgcca | tgggtcataa | caaggaagcg | catccagaaa | ctaacaaaag | agttcctgca | 360 |
| atagttgatg | ctctcgaaaa | actggagctt | acttcgaagc | atcgtggttc | acaggttctt | 420 |
| gaaattcaag | atttccaacc | tgcttcactt | gatgatattg | cactagttca | ttcaagatca | 480 |
| tacataactg | gacttgaaaa | ggctatgagt | agggcttcag | atgaaggttt | gatattcatt | 540 |
| gaaggaactg | gacctacata | tgctacccag | actactttcc | aagaatgtct | cctttctgct | 600 |
| ggtgctggaa | ttacattggt | tgattcagtg | gttgcagcat | caaagttggg | cccgaagcca | 660 |
| ccgctcggct | ttgccttagt | aaggccacca | ggacatcatg | ctgttcctga | aggtcccatg | 720 |
| ggcttctgtg | tctttgggaa | cattgcagtg | gcagctcggt | atgctcagaa | tcaacatggt | 780 |
| ttaaagcggg | tcatgataat | agattttgat | gttcaccacg | gtaacggcac | atgtgacgcc | 840 |
| ttttatgagg | atccggacat | attcttcctc | tcaactcatc | agcttggaag | ctatcctggc | 900 |
| accggtaaga | tccaccaagt | tggccagggc | aacggcgagg | gcacgacgct | caacctgcca | 960 |
| ctacccggtg | gctcaggcga | ttacgcgatg | aggtgcgcgt | tgatgaggt | tattgccca | 1020 |
| gctgcccagc | ggttcaaacc | tgacatcatc | ctcgtttcag | ccgggtacga | cgcgcacgcg | 1080 |
| ctggacccgc | tggcgggggct | gcagttcacg | acggggacgt | tctacatgct | ggcggcgagg | 1140 |
| atccgggagg | tggcggcgga | gttgtgcggc | gggcggtgcg | tcttcttcct | ggagggcggc | 1200 |
| tacaacctgg | agtcgctgtc | cagctcagtg | gccgacacct | tccgtgcgtt | cctcggcgag | 1260 |
| cccagcctcg | ccgcgcggtt | cgacgacccg | gcgatgctct | acgaggagcc | cacgcggaag | 1320 |
| atcagggagg | ccatcgacaa | ggccaagcac | ctccactcgc | tctaagcgcg | gcgcccagaa | 1380 |
| gattgcaaca | gtatctatac | ttggctgctg | aaactgcttg | ctgatgctgg | tcaacaactc | 1440 |
| aagatcatat | tcatgtcttg | ttagcttttg | cactttccag | | | 1480 |

<210> SEQ ID NO 2
<211> LENGTH: 1332
<212> TYPE: DNA
<213> ORGANISM: Oryza sativa

<400> SEQUENCE: 2

| | | | | | |
|---|---|---|---|---|---|
| atggaacagc | tgtgggtgcc | atcgcttccg | attcttggag | gaaggatatt | gcctatgctc | 60 |
| aggcactact | gtggctttgg | aagtcatcat | cccttaacct | ggagaagctt | acaaattact | 120 |
| ggaagaaaac | agaagcataa | tgggtgttgg | attgcatact | gcttaccaag | ccataatgga | 180 |
| acttctattt | cagacacaaa | tggtgttcga | aaagacttag | ctttgcctga | caatttgctt | 240 |
| cgtgatgctc | atattctcta | ttgtacatct | cctgccatgg | gtcataacaa | ggaagcgcat | 300 |
| ccagaaacta | caaaagagt | tcctgcaata | gttgatgctc | tcgaaaaact | ggagcttact | 360 |

```
tcgaagcatc gtggttcaca ggttcttgaa attcaagatt tccaacctgc ttcacttgat    420
gatattgcac tagttcattc aagatcatac ataactggac ttgaaaaggc tatgagtagg    480
gcttcagatg aaggtttgat attcattgaa ggaactggac ctacatatgc tacccagact    540
actttccaag aatgtctcct ttctgctggt gctggaatta cattggttga ttcagtggtt    600
gcagcatcaa agttgggccc gaagccaccg ctcggctttg ccttagtaag gccaccagga    660
catcatgctg ttcctgaagg tcccatgggc ttctgtgtct ttgggaacat tgcagtggca    720
gctcggtatg ctcagaatca acatggttta aagcgggtca tgataataga ttttgatgtt    780
caccacggta acggcacatg tgacgccttt tatgaggatc cggacatatt cttcctctca    840
actcatcagc ttggaagcta tcctggcacc ggtaagatcc accaagttgg ccagggcaac    900
ggcgagggca cgacgctcaa cctgccacta cccgtgggct caggcgatta cgcgatgagg    960
tgcgcgtttg atgaggttat tgccccagct gcccagcggt tcaaacctga catcatcctc   1020
gtttcagccg gtacgacgc gcacgcgctg acccgctgg cggggctgca gttcacgacg   1080
gggacgttct acatgctggc ggcgaggatc cgggaggtgg cggcggagct gtgcggcggg   1140
cggtgcgtct tcttcctgga gggcggctac aacctggagt cgctgtccag ctcagtggcc   1200
gacaccttcc gtgcgttcct cggcgagccc agcctcgccg cgcggttcga cgacccggcg   1260
atgctctacg aggagcccac gcggaagatc agggaggcca tcgacaaggc caagcacctc   1320
cactcgctct aa                                                       1332

<210> SEQ ID NO 3
<211> LENGTH: 443
<212> TYPE: PRT
<213> ORGANISM: Oryza sativa

<400> SEQUENCE: 3

Met Glu Gln Leu Trp Val Pro Ser Leu Pro Ile Leu Gly Gly Arg Ile
1               5                   10                  15

Leu Pro Met Leu Arg His Tyr Cys Gly Phe Gly Ser His His Pro Leu
            20                  25                  30

Thr Trp Arg Ser Leu Gln Ile Thr Gly Arg Lys Gln Lys His Asn Gly
        35                  40                  45

Cys Trp Ile Ala Tyr Cys Leu Pro Ser His Asn Gly Thr Ser Ile Ser
    50                  55                  60

Asp Thr Asn Gly Val Arg Lys Asp Leu Ala Leu Pro Asp Asn Leu Leu
65                  70                  75                  80

Arg Asp Ala His Ile Leu Tyr Cys Thr Ser Pro Ala Met Gly His Asn
                85                  90                  95

Lys Glu Ala His Pro Glu Thr Asn Lys Arg Val Pro Ala Ile Val Asp
            100                 105                 110

Ala Leu Glu Lys Leu Glu Leu Thr Ser Lys His Arg Gly Ser Gln Val
        115                 120                 125

Leu Glu Ile Gln Asp Phe Gln Pro Ala Ser Leu Asp Asp Ile Ala Leu
    130                 135                 140

Val His Ser Arg Ser Tyr Ile Thr Gly Leu Glu Lys Ala Met Ser Arg
145                 150                 155                 160

Ala Ser Asp Glu Gly Leu Ile Phe Ile Glu Gly Thr Gly Pro Thr Tyr
                165                 170                 175

Ala Thr Gln Thr Thr Phe Gln Glu Cys Leu Leu Ser Ala Gly Ala Gly
            180                 185                 190
```

```
Ile Thr Leu Val Asp Ser Val Val Ala Ala Ser Lys Leu Gly Pro Lys
            195                 200                 205
Pro Pro Leu Gly Phe Ala Leu Val Arg Pro Pro Gly His His Ala Val
        210                 215                 220
Pro Glu Gly Pro Met Gly Phe Cys Val Phe Gly Asn Ile Ala Val Ala
225                 230                 235                 240
Ala Arg Tyr Ala Gln Asn Gln His Gly Leu Lys Arg Val Met Ile Ile
                245                 250                 255
Asp Phe Asp Val His His Gly Asn Thr Cys Asp Ala Phe Tyr Glu
            260                 265                 270
Asp Pro Asp Ile Phe Phe Leu Ser Thr His Gln Leu Gly Ser Tyr Pro
        275                 280                 285
Gly Thr Gly Lys Ile His Gln Val Gly Gln Gly Asn Gly Glu Gly Thr
    290                 295                 300
Thr Leu Asn Leu Pro Leu Pro Gly Gly Ser Gly Asp Tyr Ala Met Arg
305                 310                 315                 320
Cys Ala Phe Asp Glu Val Ile Ala Pro Ala Gln Arg Phe Lys Pro
                325                 330                 335
Asp Ile Ile Leu Val Ser Ala Gly Tyr Asp Ala His Ala Leu Asp Pro
            340                 345                 350
Leu Ala Gly Leu Gln Phe Thr Thr Gly Thr Phe Tyr Met Leu Ala Ala
        355                 360                 365
Arg Ile Arg Glu Val Ala Ala Glu Leu Cys Gly Gly Arg Cys Val Phe
    370                 375                 380
Phe Leu Glu Gly Gly Tyr Asn Leu Glu Ser Leu Ser Ser Ser Val Ala
385                 390                 395                 400
Asp Thr Phe Arg Ala Phe Leu Gly Glu Pro Ser Leu Ala Ala Arg Phe
                405                 410                 415
Asp Asp Pro Ala Met Leu Tyr Glu Glu Pro Thr Arg Lys Ile Arg Glu
            420                 425                 430
Ala Ile Asp Lys Ala Lys His Leu His Ser Leu
        435                 440

<210> SEQ ID NO 4
<211> LENGTH: 684
<212> TYPE: DNA
<213> ORGANISM: Oryza sativa

<400> SEQUENCE: 4
catgggtgtg agtatggggc aaggaaaccc aatgggtatg cacttgttgc catctggcag      60
ctcaagtccg cgcacctcgc cttccctccg cgacccgccc tctcccctcc ccgtccttcc     120
caactccgac ctctccgtgt ccctccccga cctgcataag cttcgccgca atgagcccgt     180
cacttcgggc atcctccacg tccgcgacct ctcattcctc cgccccgca gccacaacgg      240 ggatgatgat gaggagaccg aggagatgac ccgtgagcag gaggagaagt acttgcagtg     300
gaggagctcc ctggtcgaga agctggccgg gatcgagctc aacctcgaga gggttaagtt     360
tcggatgagc gtcgaaatcc cgccctccga tgacttcagg gcaatgaaga agtcttggga     420
gaatttctac gcctccgagc tcctcagtag cagtatggaa ttcattttt aaaatgaaaa      480 tgctgctctt agttgtgatt cttcctaggt ggagtttgga ttgatgcttg ctttgttcag     540
ggaatcctgt gaggaagata gcgaaaaggc cagacacaat tcttgtccgt ggtgtgccat     600
ccaggtggtt tgcggagacg aggatatcat cgaaagcctc cacactggtc acacacacta     660
tcatcgaaag ctgctaggcc aaac                                            684
```

<210> SEQ ID NO 5
<211> LENGTH: 588
<212> TYPE: DNA
<213> ORGANISM: Oryza sativa

<400> SEQUENCE: 5

```
atgggtgtga gtatggggca aggaaaccca atgggtatgc acttgttgcc atctggcagc      60
tcaagtccgc gcacctcgcc ttccctccgc gacccgcccc tctccctccc cgtccttccc     120
aactccgacc tctccgtgtc cctccccgac ctgcataagc ttcgccgcaa tgagcccgtc     180
acttcgggca tcctccacgt ccgcgacctc tcattcctcc gccccgcag ccacaacggg     240
gatgatgatg aggagaccga ggagatgacc cgtgagcagg aggagaagta cttgcagtgg     300
aggagctccc tggtcgagaa gctggccggg atcgagctca acctcgagag ggttaagttt     360
cggatgagcg tcgaaatccc gccctccgat gacttcaggg caatgaagaa gtcttgggag     420
aatttctacg cctccgagct cctcagtagc aggaatcctg tgaggaagat agcgaaaagg     480
ccagacacaa ttcttgtccg tggtgtgcca tccaggtggt ttgcggagac gaggatatca     540
tcgaaagcct ccacactggt cacacacact atcatcgaaa gctgctag                  588
```

<210> SEQ ID NO 6
<211> LENGTH: 195
<212> TYPE: PRT
<213> ORGANISM: Oryza sativa

<400> SEQUENCE: 6

```
Met Gly Val Ser Met Gly Gln Gly Asn Pro Met Gly Met His Leu Leu
1               5                   10                  15

Pro Ser Gly Ser Ser Pro Arg Thr Ser Pro Ser Leu Arg Asp Pro
            20                  25                  30

Pro Leu Ser Leu Pro Val Leu Pro Asn Ser Asp Leu Ser Val Ser Leu
        35                  40                  45

Pro Asp Leu His Lys Leu Arg Arg Asn Glu Pro Val Thr Ser Gly Ile
    50                  55                  60

Leu His Val Arg Asp Leu Ser Phe Leu Arg Pro Arg Ser His Asn Gly
65                  70                  75                  80

Asp Asp Asp Glu Glu Thr Glu Glu Met Thr Arg Glu Gln Glu Glu Lys
                85                  90                  95

Tyr Leu Gln Trp Arg Ser Ser Leu Val Glu Lys Leu Ala Gly Ile Glu
            100                 105                 110

Leu Asn Leu Glu Arg Val Lys Phe Arg Met Ser Val Glu Ile Pro Pro
        115                 120                 125

Ser Asp Asp Phe Arg Ala Met Lys Lys Ser Trp Glu Asn Phe Tyr Ala
    130                 135                 140

Ser Glu Leu Leu Ser Ser Arg Asn Pro Val Arg Lys Ile Ala Lys Arg
145                 150                 155                 160

Pro Asp Thr Ile Leu Val Arg Gly Val Pro Ser Arg Trp Phe Ala Glu
                165                 170                 175

Thr Arg Ile Ser Ser Lys Ala Ser Thr Leu Val Thr His Thr Ile Ile
            180                 185                 190

Glu Ser Cys
        195
```

<210> SEQ ID NO 7
<211> LENGTH: 7916

<212> TYPE: DNA
<213> ORGANISM: Oryza sativa

<400> SEQUENCE: 7

| | | | | | |
|---|---|---|---|---|---|
| cccatccttc | tctctctcca | cctaaggctc | gaatcgaagc | cgacctcctc | ctccgctcgc | 60 |
| cgccgccgcc | ggcgtcgtcc | gcggcgagat | ggcgccgccc | ttcgtcttcc | cctcgaccct | 120 |
| ccgggacctg | gagcgggacg | gagacggcgg | cggcgacgac | gagccggccc | tccgcccgca | 180 |
| gaaccccgtc | gccgtcggcg | cactccgcgc | cgccgacctc | gaggagttcg | tcaaaggtat | 240 |
| aaaacccgct | ccccaccacc | tccgcttcct | ctcgaaatca | ctccatcgct | tgccgtaaat | 300 |
| cgatggtttg | gttgtggcgt | gcggtggagc | tgagattgtt | tctcctgtat | cgttcgcttc | 360 |
| gtattggtgg | ttgtaaagtg | taaaccctag | ttcccgttaa | tttggcctcc | cgcgctctac | 420 |
| tcctagtttg | gttcttgcat | gtatttaaga | cccaattaaa | gtcaaatccc | tgtgattctg | 480 |
| tggaataaga | gttgtggact | gttgatagac | attttttggcg | caagattttg | ctgcatttag | 540 |
| cctgtagagt | catttcaaag | ctaactattg | caaggcatat | cctttttaga | attttttttc | 600 |
| atcttgctcc | ttggccattt | tcatcgaagt | ggattgttta | tttgttttgc | ttttagaatc | 660 |
| tgcagctttg | gatatgacag | ggtttagcta | gctcatgtgt | agtaatggaa | ctaacaattg | 720 |
| agtgttcttg | cttttgacaa | aaggttcggc | ctctatttgt | gtcccacaaa | aaaagtttt | 780 |
| ttcttctaca | tgttaaaatt | cgttagacca | gggagctttg | tggcatgtag | ggaaattaat | 840 |
| gcacatgttt | gtaagaaaaa | catgcacatt | catctgtgca | tctgtaaata | tttcaaactg | 900 |
| tgaaatgata | ccatccttac | ctagctctgg | gctatgaatg | ccttttgtaa | gtttcatctc | 960 |
| cattcctctt | cctggaaaag | tttgttttta | ttttaggcat | tcacatcacc | aaaactgacg | 1020 |
| attcattcaa | ggacatcaga | caaaaagttt | tagtcccatt | catctattca | tccaaactta | 1080 |
| caaagctttt | actgggctaa | aatttctcaa | tgtgcatttt | gtcacaaact | agtgcatatt | 1140 |
| aagcttaatg | taagctgcat | gtggtttgtt | cagcaaagta | ttcaatttat | ctcacaatca | 1200 |
| aagtactaac | tcttattgaa | tcaattttgt | aatattccac | cctgtttgaa | tgagcgtgca | 1260 |
| gctgtgcatt | ttacatcgtg | tatcttttga | accaaaggtt | ttctctgaac | gagctaattc | 1320 |
| tttctttcat | tttttttctt | aaattatagg | cacatcgttt | gacctgtctg | acaaggaact | 1380 |
| cttctgcatc | gaggagcagg | acgtatttga | ccgcgtctat | tccctcgtgc | gtgacttcac | 1440 |
| ttgcttgccc | cctgccctca | agttcaacct | tgttgagacc | ttgcgctcca | atcttagtgt | 1500 |
| tctcctccca | aacatagact | cccttttcacg | agcttccatg | tcatcccctt | ctgatgggat | 1560 |
| cccagtaact | gatcgcattg | cttcgcatcg | gaatgccctt | aagatctact | ccttcttcct | 1620 |
| cctctccatt | gttgttgctg | aagaatcggg | agctgatagt | tgcaatggcc | ctaaggtaat | 1680 |
| acctgtgcaa | aagttacaat | ttatttggac | tctttgtacc | cttctaattt | taactgaact | 1740 |
| tattatgcca | tgtggactta | ggtggcagta | catggtcgga | agaagaatgc | tgtatatgct | 1800 |
| tggaattggg | aagcacaaag | aggccgcatc | atgaatctta | ttgctaattc | acttgaagtt | 1860 |
| gacctatcac | tattgtttgg | tccaggcggt | gctgatgaac | aatatctctc | ttttgtttca | 1920 |
| aagtaaattc | aagaaactag | ctgtgttatg | ctttctgtat | tcattcctta | tagagttata | 1980 |
| gtgatgttgc | tttggatgaa | tatgtgtagg | tgtacttttg | ttctctgtga | gaaccagaac | 2040 |
| gtgctgaaag | atgaggaaat | aagaaatggc | ttgtgccgaa | taattggtgc | aattgctacg | 2100 |
| aagcatcaaa | gagtatctca | aacaagtgca | tctgtcttgc | atttgattca | taaatttgat | 2160 |
| ttcactgtcg | tgcttctagc | ggaatcagtt | gctgctgcag | agaaaaggtt | tggtgatgga | 2220 |

```
agccttgcga ttttgctgat aagggaaata ggtcggactg acccaaaaga ttatgtaaga    2280
gatagtgccg gtgctgacaa tgccgggaga ttcctagtag aacttgcaga tcgcttgcca    2340
aagctcatgt caaccaatat tggtgttctg atacctcatt ttggtgggga atcatacaag    2400
attagaaatt ctcttgttgg ggtcttgggc aagctggctg caaaggcctt caaagatgtt    2460
gaaggcgata gtgacgccca ttctttaagg ctccgaagta agcatgctat gctggaaatt    2520
ttgcttgaac gttgtcgaga tgtgtctgca tacacgagga gtcgtgtgct tcaggtatgg    2580
gcagagctgt gtgaagaaaa tgctatttca attggcctgt ggaatgaagt ggcatcagtt    2640
gcttcgggca gactggagga caagagtgca attgtgagaa atcagcact gcaattactc     2700 atcacaatgc tgcagcacaa tccttttggg cctcaactaa ggactgcaac ctttgaggca    2760
actctagaaa ggtacaagga gaaattgcaa ggaatggagc ctccttctcc cgagaaggat    2820
gagctcttga atgattcttc actgggtgaa gtgattgcag ggcaggatga aagtgtcagt    2880
gatagctgtt taccttctag tcaagaccca aaggatcaag atcccacaat tgtggatata    2940
acaaacttgg aacagattag agctttagtt gcatcacttg aggctggtct gagattctcg    3000
gcatgtataa cttcattaat gccaactctt gtccagttgt tggcatcgtc ttcagccact    3060
gatgttgaga acacaattct tctattaatg agatgcagac aatttcagat tgaaggttcg    3120
gaagaagccc tccggaaaat gttacctctg gtaatgcctc cctggaagtg taggttgttt    3180
gtgaatatga gttagaatgt acacttcgtc acttccttat cttcataaat tttgcaggta    3240
ttttctcagg ataagtcaat atatgaagct gtggagagtg cattcatcac tatatacaca    3300
aagaaaagtc ccacggaaac agccaaaagt ttattaaacc ttaccattga atgcagcatt    3360
ggtgaccttg ctgcccttga aagcttagtt agttcattgg tatcaaaagg agaaatttca    3420
tccaacacgg tgcactcttg tttcccttca aagtttgctc atagcaacct ttcaaatgct    3480 atttttaca gtttagttac agtaatgcta agtactcccc ccattccaaa atatagggca     3540
caacgatttt ttcccctaat gttgcataat acgaggttcg catgcatgcg tgcatgctat    3600
tgactagcac ctccccctcc tctaagttct atttttaaag cctctaccct caagatctct    3660
gatctctaat cccattgggt gcatgcattt tatttattgg gatgatccaa attagaaggt    3720
gataataatt ttttcttggt ttttgcgtaa gagatagttg ctcattatat tttggaatgt    3780 agggagtac tcatttattc tagcacacca atctcctgtg caccaaaagt gattctgcac      3840
atagattgag aatgcaaggt agtactaact tgcaattaag tgagtgcatt aattgctgaa    3900
tatgcataaa ttaagaactt aagatgcatg caaagaatat tgctcccagt ttctccactt    3960
tctgatgtga acttccctta tctagatcct acagtgggaa cttttttctg ttcatcttga    4020
agtatctttt gttagctgct catcaaaata atttatattg cctataacat aacttatacc    4080
attttgtcga atgttattta tctaacttca gtgacaccta ttatcttttg ttggggaagt    4140
tcacacttgt taaatcccat tgtcttttgc agataacagc cctgtgggat tattttgct     4200 ttcacatcaa tggtgtgaaa ccagtgcaaa gccgtggagc tttatcgatt ctttgcatgg    4260
cagcaaagtc atctcccagc attttgggta ctcatttgca agatattatt gatattgggt    4320
ttggacgctg ggctaaggag gagcctctgc ttgctagaac tgcatgcatt gccctgcaaa    4380
gattatccaa tgaagacaaa gtcaaattaa ttagtactgg tagtagggta ttcgctgcat    4440
tgcaaggcct gataactagc ctctcacttc ctgagaaaat atggtatgga gccgcagata    4500
aagctataag tgccatctac gctttacacc cagcacctga atcttcgct gctcagattg      4560 taaagaaatc acttaattct gtattcggtg tcttaggaac tgattgcatg tcaaatgaaa    4620
```

```
atgaaactca gaatggttcc atgctgtcat cgacaccagc cacaaatctg ggcagatttc   4680
ttttcattat tagtcatata gcactgaatc atttggttta cattgagact tctgttaaga   4740
aaattcagaa acagaaacgg aagaatgaca atcagagcc tactgccgag gatcttcagg    4800
cagatgcctc caaaaattcg gaggtatttt atttcttagt ttgctttgtg gcctaatcga   4860
ttttgggtta ccattctttc gtctgagtgt gtattgcact tctcttttac tgtgtgatgc   4920
tggcaggcac aaggtataaa tgctgagttg ggaattggtg catctgtaga tattgcaata   4980
gagtccctcg ctgaaaaggc agaaagggag attgtgtcca attctgaaaa gaatcttatt   5040
ggatactgtg caccatttct cgcaaaactc tgcaggaacc tggctttgct tcaaaaggtc   5100
ctaatttgta ttgagcttcc tttatttct taatgttttg actctactac tctctgtttt    5160
ttgttcctta cttttttgtt aatgcagttt ccagggttac aggcctctgc aatgcttgct   5220
ctttgcaagc taatgattat tgatgcagaa ttctggtaag tatatattta tattccagct   5280
gtttcacctt ttcaatatga tgtgctccag atatttatat tccatcaaat gctcaacttt   5340
cagtgaagca aatcttcaga tcctatttac tgctgctgag agcgcgcctt ctgaagttgt   5400
ccgatcaaac tgcactatag ctcttggtga tttagtggtt cgcttttccaa acctcttaga  5460 accttggaca gagcacatat atgcacgctt acgtgatcct tcggcatctg tgaggaagaa   5520
cactgtgctt gtcatttcac atcttatatt gaatgatatg atgaaggtct ctctctctct   5580
ctctctctct ctctctcgtg tgtgtgtgtg tgtgtgtttg ttcgaacacc atgcccctct   5640
cagttttata tttaaacatc tttgcaaaat atttataggt taaaggcttt attaatgaaa   5700
tggccgtaag gatagaagat gaagacgaga ggatctcaag ccttgcaaaa ctcttctttc   5760
atgagttatc aaagaaaggc atgtccagca aatgtgtcgg tcaaataaat tgcgtaactt   5820
gaatatacat gtttgactta tctgacgttt agttcttttt ctttttgatc tttttaggaa   5880
gcaatccaat ttataatctt cttccggata tcctgggtag attgtgcaat caacaactca   5940
aggatgaaac gttctgcagc attatgcaat tcttgatcag ctctattaaa aaggtataag   6000
cataactttt tttctgtttt cagcaattac tatgctttaa ctgtactttg agtaactata   6060
tacatttcta actgcattct caggacaaac aaatggaagc tcttgtggat aagctctgca   6120
atagatttgc tggtgtaaat ggtactatgc atatacctg catctatatt cgttcgagct    6180
ttcccatcta aggctaatca actaccattg cttctgtatt caagatacca tgacataaat   6240
aatattactt cctccgtttc atattataag attttctagc attgcccgta ttcatataga   6300
tgttaatgaa tctaaacata tatatgtgtc tagattcatt aatatctata cgaatgtaga   6360
caatgctaga aagtcttata acctgaaacg gaggtagtaa atgagtggca atgatattta   6420
catggaaaat gtgagcacac atcagaaacg gaatgttgtg atgcagcatt cttgttcttt   6480
gttgcaacct tgtagtggag tggcttttgc ataagctagc aatatgggaa gctagtgagc   6540
caatttgatt tattttcact cctttcattt taatcctgtc ttgagatttc tgaattttca   6600
catgcaatat ttcaacattt atgaatgatt gaattgttgt gatcccattt tcagatcctt   6660
gacctttctt tttgttgtgt ttcagatgtt agacagtggg agtatatatc ctattgcctt   6720
tctcagctga ctttcacaga gaagggtttg aaaaaactag ttgataattt caagatattt   6780
gagcatgcat tatctgaaga ttctgtaatg aaccacttca gaactgtgat agcaaaggtt   6840
ggtgctcagt agcctaggct gaatggatgc atatgttatt atgttaaata cagcagggct   6900
gaatttgtga actcttcaat gttttttttaa tctatggtaa ttcctcctat cagtgcaaga   6960
```

```
agtttgccaa gccagatctc aaagtttgca ttgaggaatt tgatgagaaa ctcagcaagg      7020
ttcatcagga aaagaaagag caagaggcca cgaccaggaa tgccgaggca cacaaacaaa      7080
gaattggttc acttgacaaa ctcatggtaa ctaagagaac tgggaaggat aagggaaaat      7140
ctgctgaagg tacaattttt tttctctgaa tctccttatc atctatatca tttaagttaa      7200
tctccacatg atcatccatc atgtattgac tatgaactca acattagat tagaataagg       7260 ttacgctgta aatctgtgtc tataatctat acaccagaaa aattgatgct taccttaaac      7320
tgaggttcat ttctttctgt ctgtcagtgg cagaggaaac tagtgaggta gttgatccat      7380
caacggagag caattctgaa gataaggaga acatgccaga atgcagtgac aatatttgtt      7440
cggaaaagag tcatacatca tccacgttta cagaatcaga cggtgacagc acagaggttc      7500
aatcagcgag aacttcttgc aaaggtaaca gatggttgca ctgctgatat tcgcatgaca      7560
catccagttt ctcaaggaat ctgttccatg cattatgcag gcgtgtcgcg ttcaaggata      7620
aataaaatga gagaaccgga agactcagaa gacagtgctc caatgagacg tgtgtctcgc      7680
agaaggtgtt tacactcact accttacaac aatcttactt catagtagta gtatttgttt      7740
cacgtccact aatttttaaat ctttctggat cattgctttg ttcatactac taagcagtgc      7800
tattagactc gtccttaatt cctactcatg aattactaag aaatgcattt gcttacaaac      7860
tttgcagacc agttaggtga tgccgaactg taatatggac caggtggcaa caactc         7916

<210> SEQ ID NO 8
<211> LENGTH: 3978
<212> TYPE: DNA
<213> ORGANISM: Oryza sativa

<400> SEQUENCE: 8
atggcgccgc ccttcgtctt ccctcgacc ctccgggacc tggagcggga cggagacggc        60
ggcggcgacg acgagccggc cctccgcccg cagaaccccg tcgccgtcgg cgcactccgc       120
gccgccgacc tcgaggagtt cgtcaaaggc acatcgtttg acctgtctga caaggaactc       180
ttctgcatcg aggagcagga cgtgtttgac cgcgtctatt ccctcgtgcg tgacttcact       240
tgcttgcccc ctgccctcaa gttcaaccttg ttgagacctt gcgctccaa tcttagtgtt       300 ctcctcccaa acatagactc cctttcacga gcttccatgt catcccttc tgatgggatc       360 ccagtaactg atcgcattgc ttcgcatcgg aatgccctta agatctactc cttcttcctc       420
ctctccattg ttgttgctga agaatcggga gctgatagtt gcaatggccc taaggtggca       480
gtacatggtc ggaagaagaa tgctgtatat gcttggaatt gggaagcaca agaggccgc        540 atcatgaatc ttattgctaa ttcacttgaa gttgacctat cactattgtt tggtccaggc       600
ggtgctgatg aacaatatct ctcttttgtt tcaaagtgta cttttgttct ctgtgagaac       660
cagaacgtgc tgaaagatga ggaaataaga aatggcttgt gccgaataat tggtgcaatt       720
gctacgaagc atcaaagagt atctcaaaca agtgcatctg tcttgcattt gattcataaa       780
tttgatttca ctgtcgtgct tctagcggaa tcagttgctg ctgcagagaa aaggtttggt       840
gatggaagcc ttgcgatttt gctgataagg gaaataggtc ggactgaccc aaaagattat      900
gtaagagata gtgccggtgc tgacaatgcc gggagattcc tagtagaact tgcagatcgc      960
ttgccaaagc tcatgtcaac caatattggt gttctgatac ctcattttgg tggggaatca     1020
tacaagatta gaaattctct tgttggggtc ttgggcaagc tggctgcaaa ggccttcaaa     1080
gatgttgaag gcgatagtga cgcccattct ttaaggctcc gaagtaagca tgctatgctg     1140
gaaattttgc ttgaacgttg tcgagatgtg tctgcataca cgaggagtcg tgtgcttcag     1200
```

```
gtatgggcag agctgtgtga agaaaatgct atttcaattg gcctgtggaa tgaagtggca   1260
tcagttgctt cgggcagact ggaggacaag agtgcaattg tgagaaaatc agcactgcaa   1320
ttactcatca caatgctgca gcacaatcct tttgggcctc aactaaggac tgcaaccttt   1380
gaggcaactc tagaaaggta caaggagaaa ttgcaaggaa tggagcctcc ttctcccgag   1440
aaggatgagc tcttgaatga ttcttcactg ggtgaagtga ttgcagggca ggatgaaagt   1500
gtcagtgata gctgtttacc ttctagtcaa gacccaaagg atcaagatcc cacaattgtg   1560
gatataacaa acttggaaca gattagagct ttagttgcat cacttgaggc tggtctgaga   1620
ttctcggcat gtataacttc attaatgcca actcttgtcc agttgttggc atcgtcttca   1680
gccactgatg ttgagaacac aattcttcta ttaatgagat gcagacaatt cagattgaa    1740 ggttcggaag aagccctccg gaaaatgtta cctctggtat tttctcagga taagtcaata   1800
tatgaagctg tggagagtgc attcatcact atatacacaa agaaaagtcc cacggaaaca   1860
gccaaaagtt tattaaacct taccattgaa tgcagcattg tgaccttgc tgcccttgaa    1920 agcttagtta gttcattggt atcaaaagga gaaatttcat ccaacacgat aacagccctg   1980
tgggattatt tttgctttca catcaatggt gtgaaaccag tgcaaagccg tggagcttta   2040
tcgattcttt gcatggcagc aaagtcatct cccagcattt gggtactca tttgcaagat    2100 attattgata ttgggtttgg acgctgggct aaggaggagc ctctgcttgc tagaactgca   2160
tgcattgccc tgcaaagatt atccaatgaa gacaaagtca aattaattag tactggtagt   2220
agggtattcg ctgcattgca aggcctgata actagcctct cacttcctga gaaaatatgg   2280
tatggagccg cagataaagc tataagtgcc atctacgctt tacacccagc acctgaaatc   2340
ttcgctgctc agattgtaaa gaaatcactt aattctgtat cggtgtctt aggaactgat    2400 tgcatgtcaa atgaaaatga aactcagaat ggttccatgc tgtcatcgac accagccaca   2460
aatctgggca gatttctttt cattattagt catatagcac tgaatcattt ggtttacatt   2520
gagacttctg ttaagaaaat tcagaaacag aaacggaaga atgacaaatc agagcctact   2580
gccgaggatc ttcaggcaga tgcctccaaa aattcggagg cacaaggtat aaatgctgag   2640
ttgggaattg gtgcatctgt agatattgca atagagtccc tcgctgaaaa ggcagaaagg   2700
gagattgtgt ccaattctga aaagaatctt attggatact gtgcaccatt tctcgcaaaa   2760
ctctgcagga acctggcttt gcttcaaaag tttccagggt tacaggcctc tgcaatgctt   2820
gctctttgca agctaatgat tattgatgca gaattctgtg aagcaaatct tcagatccta   2880
tttactgctg ctgagagcgc gccttctgaa gttgtccgat caaactgcac tatagctctt   2940
ggtgatttag tggttcgctt tccaaacctc ttagaacctt ggacagagca catatatgca   3000
cgcttacgtg atccttcggc atctgtgagg aagaacactg tgcttgtcat ttcacatctt   3060
atattgaatg atatgatgaa ggttaaaggc tttattaatg aaatggccgt aaggatagaa   3120
gatgaagacg agaggatctc aagccttgca aaactcttct ttcatgagtt atcaaagaaa   3180
ggaagcaatc caatttataa tcttcttccg gatatcctgg gtagattgtg caatcaacaa   3240
ctcaaggatg aaacgttctg cagcattatg caattcttga tcagctctat taaaaaggac   3300
aaacaaatgg aagctcttgt ggataagctc tgcaatagat ttgctggtgt aaatgatgtt   3360
agacagtggg agtatatatc ctattgcctt tctcagctga cttccacaga aagggttg     3420 aaaaaactag ttgataattt caagatattt gagcatgcat tatctgaaga ttctgtaatg   3480
aaccacttca gaactgtgat agcaaagtgc aagaagtttg ccaagccaga tctcaaagtt   3540
```

```
tgcattgagg aatttgatga gaaactcagc aaggttcatc aggaaaagaa agagcaagag    3600
gccacgacca ggaatgccga ggcacacaaa caaagaattg gttcacttga caaactcatg    3660
gtaactaaga gaactgggaa ggataaggga aaatctgctg aagtggcaga ggaaactagt    3720
gaggtagttg atccatcaac ggagagcaat tctgaagata aggagaacat gccagaatgc    3780
agtgacaata tttgttcgga aaagagtcat acatcatcca cgtttacaga atcagacggt    3840
gacagcacag aggttcaatc agcgagaact tcttgcaaag gcgtgtcgcg ttcaaggata    3900
aataaaatga gagaaccgga agactcagaa gacagtgctc caatgagacg tgtgtctcgc    3960
agaagaccag ttaggtga                                                 3978

<210> SEQ ID NO 9
<211> LENGTH: 1325
<212> TYPE: PRT
<213> ORGANISM: Oryza sativa

<400> SEQUENCE: 9
```

Met Ala Pro Pro Phe Val Phe Pro Ser Thr Leu Arg Asp Leu Glu Arg
1               5                   10                  15

Asp Gly Asp Gly Gly Asp Asp Glu Pro Ala Leu Arg Pro Gln Asn
            20                  25                  30

Pro Val Ala Val Gly Ala Leu Arg Ala Ala Asp Leu Glu Glu Phe Val
        35                  40                  45

Lys Gly Thr Ser Phe Asp Leu Ser Asp Lys Glu Leu Phe Cys Ile Glu
    50                  55                  60

Glu Gln Asp Val Phe Asp Arg Val Tyr Ser Leu Val Arg Asp Phe Thr
65                  70                  75                  80

Cys Leu Pro Pro Ala Leu Lys Phe Asn Leu Val Glu Thr Leu Arg Ser
                85                  90                  95

Asn Leu Ser Val Leu Leu Pro Asn Ile Asp Ser Leu Ser Arg Ala Ser
            100                 105                 110

Met Ser Ser Pro Ser Asp Gly Ile Pro Val Thr Asp Arg Ile Ala Ser
        115                 120                 125

His Arg Asn Ala Leu Lys Ile Tyr Ser Phe Phe Leu Leu Ser Ile Val
    130                 135                 140

Val Ala Glu Glu Ser Gly Ala Asp Ser Cys Asn Gly Pro Lys Val Ala
145                 150                 155                 160

Val His Gly Arg Lys Lys Asn Ala Val Tyr Ala Trp Asn Trp Glu Ala
                165                 170                 175

Gln Arg Gly Arg Ile Met Asn Leu Ile Ala Asn Ser Leu Glu Val Asp
            180                 185                 190

Leu Ser Leu Leu Phe Gly Pro Gly Gly Ala Asp Glu Gln Tyr Leu Ser
        195                 200                 205

Phe Val Ser Lys Cys Thr Phe Val Leu Cys Glu Asn Gln Asn Val Leu
    210                 215                 220

Lys Asp Glu Glu Ile Arg Asn Gly Leu Cys Arg Ile Ile Gly Ala Ile
225                 230                 235                 240

Ala Thr Lys His Gln Arg Val Ser Gln Thr Ser Ala Ser Val Leu His
                245                 250                 255

Leu Ile His Lys Phe Asp Phe Thr Val Val Leu Ala Glu Ser Val
            260                 265                 270

Ala Ala Ala Glu Lys Arg Phe Gly Asp Gly Ser Leu Ala Ile Leu Leu
        275                 280                 285

Ile Arg Glu Ile Gly Arg Thr Asp Pro Lys Asp Tyr Val Arg Asp Ser

```
                290                 295                 300
Ala Gly Ala Asp Asn Ala Gly Arg Phe Leu Val Glu Leu Ala Asp Arg
305                 310                 315                 320
Leu Pro Lys Leu Met Ser Thr Asn Ile Gly Val Leu Ile Pro His Phe
                325                 330                 335
Gly Gly Glu Ser Tyr Lys Ile Arg Asn Ser Leu Val Gly Val Leu Gly
                340                 345                 350
Lys Leu Ala Ala Lys Ala Phe Lys Asp Val Glu Gly Asp Ser Asp Ala
                355                 360                 365
His Ser Leu Arg Leu Arg Ser Lys His Ala Met Leu Glu Ile Leu Leu
        370                 375                 380
Glu Arg Cys Arg Asp Val Ser Ala Tyr Thr Arg Ser Arg Val Leu Gln
385                 390                 395                 400
Val Trp Ala Glu Leu Cys Glu Glu Asn Ala Ile Ser Ile Gly Leu Trp
                405                 410                 415
Asn Glu Val Ala Ser Val Ala Ser Gly Arg Leu Glu Asp Lys Ser Ala
                420                 425                 430
Ile Val Arg Lys Ser Ala Leu Gln Leu Leu Ile Thr Met Leu Gln His
                435                 440                 445
Asn Pro Phe Gly Pro Gln Leu Arg Thr Ala Thr Phe Glu Ala Thr Leu
        450                 455                 460
Glu Arg Tyr Lys Glu Lys Leu Gln Gly Met Glu Pro Pro Ser Pro Glu
465                 470                 475                 480
Lys Asp Glu Leu Leu Asn Asp Ser Ser Leu Gly Glu Val Ile Ala Gly
                485                 490                 495
Gln Asp Glu Ser Val Ser Asp Ser Cys Leu Pro Ser Ser Gln Asp Pro
                500                 505                 510
Lys Asp Gln Asp Pro Thr Ile Val Asp Ile Thr Asn Leu Glu Gln Ile
                515                 520                 525
Arg Ala Leu Val Ala Ser Leu Glu Ala Gly Leu Arg Phe Ser Ala Cys
        530                 535                 540
Ile Thr Ser Leu Met Pro Thr Leu Val Gln Leu Leu Ala Ser Ser Ser
545                 550                 555                 560
Ala Thr Asp Val Glu Asn Thr Ile Leu Leu Leu Met Arg Cys Arg Gln
                565                 570                 575
Phe Gln Ile Glu Gly Ser Glu Glu Ala Leu Arg Lys Met Leu Pro Leu
                580                 585                 590
Val Phe Ser Gln Asp Lys Ser Ile Tyr Glu Ala Val Glu Ser Ala Phe
                595                 600                 605
Ile Thr Ile Tyr Thr Lys Lys Ser Pro Thr Glu Thr Ala Lys Ser Leu
        610                 615                 620
Leu Asn Leu Thr Ile Glu Cys Ser Ile Gly Asp Leu Ala Ala Leu Glu
625                 630                 635                 640
Ser Leu Val Ser Ser Leu Val Ser Lys Gly Glu Ile Ser Ser Asn Thr
                645                 650                 655
Ile Thr Ala Leu Trp Asp Tyr Phe Cys Phe His Ile Asn Gly Val Lys
                660                 665                 670
Pro Val Gln Ser Arg Gly Ala Leu Ser Ile Leu Cys Met Ala Ala Lys
                675                 680                 685
Ser Ser Pro Ser Ile Leu Gly Thr His Leu Gln Asp Ile Ile Asp Ile
        690                 695                 700
Gly Phe Gly Arg Trp Ala Lys Glu Glu Pro Leu Leu Ala Arg Thr Ala
705                 710                 715                 720
```

```
Cys Ile Ala Leu Gln Arg Leu Ser Asn Glu Asp Lys Val Lys Leu Ile
            725                 730                 735

Ser Thr Gly Ser Arg Val Phe Ala Ala Leu Gln Gly Leu Ile Thr Ser
            740                 745                 750

Leu Ser Leu Pro Glu Lys Ile Trp Tyr Gly Ala Ala Asp Lys Ala Ile
            755                 760                 765

Ser Ala Ile Tyr Ala Leu His Pro Ala Pro Glu Ile Phe Ala Ala Gln
            770                 775                 780

Ile Val Lys Lys Ser Leu Asn Ser Val Phe Gly Val Leu Gly Thr Asp
785                 790                 795                 800

Cys Met Ser Asn Glu Asn Glu Thr Gln Asn Gly Ser Met Leu Ser Ser
            805                 810                 815

Thr Pro Ala Thr Asn Leu Gly Arg Phe Leu Phe Ile Ile Ser His Ile
            820                 825                 830

Ala Leu Asn His Leu Val Tyr Ile Glu Thr Ser Val Lys Lys Ile Gln
            835                 840                 845

Lys Gln Lys Arg Lys Asn Asp Lys Ser Glu Pro Thr Ala Glu Asp Leu
            850                 855                 860

Gln Ala Asp Ala Ser Lys Asn Ser Glu Ala Gln Gly Ile Asn Ala Glu
865                 870                 875                 880

Leu Gly Ile Gly Ala Ser Val Asp Ile Ala Ile Glu Ser Leu Ala Glu
            885                 890                 895

Lys Ala Glu Arg Glu Ile Val Ser Asn Ser Glu Lys Asn Leu Ile Gly
            900                 905                 910

Tyr Cys Ala Pro Phe Leu Ala Lys Leu Cys Arg Asn Leu Ala Leu Leu
            915                 920                 925

Gln Lys Phe Pro Gly Leu Gln Ala Ser Ala Met Leu Ala Leu Cys Lys
            930                 935                 940

Leu Met Ile Ile Asp Ala Glu Phe Cys Glu Ala Asn Leu Gln Ile Leu
945                 950                 955                 960

Phe Thr Ala Ala Glu Ser Ala Pro Ser Glu Val Val Arg Ser Asn Cys
            965                 970                 975

Thr Ile Ala Leu Gly Asp Leu Val Arg Pro Asn Leu Leu Glu
            980                 985                 990

Pro Trp Thr Glu His Ile Tyr Ala Arg Leu Arg Asp Pro Ser Ala Ser
            995                 1000                1005

Val Arg Lys Asn Thr Val Leu Val Ile Ser His Leu Ile Leu Asn
            1010                1015                1020

Asp Met Met Lys Val Lys Gly Phe Ile Asn Glu Met Ala Val Arg
            1025                1030                1035

Ile Glu Asp Glu Asp Glu Arg Ile Ser Ser Leu Ala Lys Leu Phe
            1040                1045                1050

Phe His Glu Leu Ser Lys Lys Gly Ser Asn Pro Ile Tyr Asn Leu
            1055                1060                1065

Leu Pro Asp Ile Leu Gly Arg Leu Cys Asn Gln Gln Leu Lys Asp
            1070                1075                1080

Glu Thr Phe Cys Ser Ile Met Gln Phe Leu Ile Ser Ser Ile Lys
            1085                1090                1095

Lys Asp Lys Gln Met Glu Ala Leu Val Asp Lys Leu Cys Asn Arg
            1100                1105                1110

Phe Ala Gly Val Asn Asp Val Arg Gln Trp Glu Tyr Ile Ser Tyr
            1115                1120                1125
```

| Cys | Leu | Ser | Gln | Leu | Thr | Phe | Thr | Glu | Lys | Gly | Leu | Lys | Lys | Leu |
| --- | --- | --- | --- | --- | --- | --- | --- | --- | --- | --- | --- | --- | --- | --- |
| | 1130 | | | | | 1135 | | | | | 1140 | | | |
| Val | Asp | Asn | Phe | Lys | Ile | Phe | Glu | His | Ala | Leu | Ser | Glu | Asp | Ser |
| 1145 | | | | | 1150 | | | | | 1155 | | | | |
| Val | Met | Asn | His | Phe | Arg | Thr | Val | Ile | Ala | Lys | Cys | Lys | Lys | Phe |
| | 1160 | | | | | 1165 | | | | | 1170 | | | |
| Ala | Lys | Pro | Asp | Leu | Lys | Val | Cys | Ile | Glu | Glu | Phe | Asp | Glu | Lys |
| | 1175 | | | | | 1180 | | | | | 1185 | | | |
| Leu | Ser | Lys | Val | His | Gln | Glu | Lys | Lys | Glu | Gln | Glu | Ala | Thr | Thr |
| | 1190 | | | | | 1195 | | | | | 1200 | | | |
| Arg | Asn | Ala | Glu | Ala | His | Lys | Gln | Arg | Ile | Gly | Ser | Leu | Asp | Lys |
| | 1205 | | | | | 1210 | | | | | 1215 | | | |
| Leu | Met | Val | Thr | Lys | Arg | Thr | Gly | Lys | Asp | Lys | Gly | Lys | Ser | Ala |
| | 1220 | | | | | 1225 | | | | | 1230 | | | |
| Glu | Val | Ala | Glu | Glu | Thr | Ser | Glu | Val | Val | Asp | Pro | Ser | Thr | Glu |
| | 1235 | | | | | 1240 | | | | | 1245 | | | |
| Ser | Asn | Ser | Glu | Asp | Lys | Glu | Asn | Met | Pro | Glu | Cys | Ser | Asp | Asn |
| | 1250 | | | | | 1255 | | | | | 1260 | | | |
| Ile | Cys | Ser | Glu | Lys | Ser | His | Thr | Ser | Ser | Thr | Phe | Thr | Glu | Ser |
| | 1265 | | | | | 1270 | | | | | 1275 | | | |
| Asp | Gly | Asp | Ser | Thr | Glu | Val | Gln | Ser | Ala | Arg | Thr | Ser | Cys | Lys |
| | 1280 | | | | | 1285 | | | | | 1290 | | | |
| Gly | Val | Ser | Arg | Ser | Arg | Ile | Asn | Lys | Met | Arg | Glu | Pro | Glu | Asp |
| | 1295 | | | | | 1300 | | | | | 1305 | | | |
| Ser | Glu | Asp | Ser | Ala | Pro | Met | Arg | Arg | Val | Ser | Arg | Arg | Arg | Pro |
| | 1310 | | | | | 1315 | | | | | 1320 | | | |
| Val | Arg | | | | | | | | | | | | | |
| | 1325 | | | | | | | | | | | | | |

<210> SEQ ID NO 10
<211> LENGTH: 635
<212> TYPE: DNA
<213> ORGANISM: Oryza sativa

<400> SEQUENCE: 10

```
gaggtggcgg agtttgtgga gatggcggtc gcggtgctcg tggaggtggc ggcagtcatg    60
gacgaagcgg aggaggcgcc gggcgcggag gcgaggcggc ggctggatct gagtggagcg   120
gcggcggtgc tagcggaggt ggcggtcgcg gatgagcggc ggcactcgtg gaggcggcgg   180
cggcggccgt ggaggcgagg cggcgctcgt ggacgcgcgg aggtggcggc ggtgctcgca   240
gaggtagtgg tcgcggacga gcggcggagc tcgtggaggc ggctgcggcg gccgcggagg   300
cgaggcggcg ctcgtggacg cgcggaggtg gtggtcgcgg gcaagcggcg gcgctcatgg   360
aggcggcggc ggtcgcggac gaggcagagg cggcggcgct caaggaggcg gcggcggcgg   420
agaaggacgt gcggaggtgg cggcgggtgt ggacgaggcg gcgacgctcg tgggcgcccg   480
gcggagctcg cgaaggtggt ggatggcgcg gtgacgccgt cgctcgtccc aggtgggacg   540
agtttgtccg ccagttttg gcggatcggt tggtcccgga tctgagagga atattcctct   600
ccagggacca acccatccca tccaccccta aaccg                              635
```

<210> SEQ ID NO 11
<211> LENGTH: 564
<212> TYPE: DNA
<213> ORGANISM: Oryza sativa

<400> SEQUENCE: 11

```
atggcggtcg cggtgctcgt ggaggtggcg gcagtcatgg acgaagcgga ggaggcgccg      60
ggcgcggagg cgaggcggcg gctggatctg agtggagcgg cggcggtgct agcggaggtg     120
gcggtcgcgg atgagcggcg gcactcgtgg aggcggcggc ggcggccgtg gaggcgaggc     180
ggcgctcgtg gacgcgcgga ggtggcggcg gtgctcgcag aggtagtggt cgcggacgag     240
cggcggagct cgtggaggcg gctgcggcgg ccgcggaggc gaggcggcgc tcgtggacgc     300
gcggaggtgg tggtcgcggg caagcggcgg cgctcatgga ggcggcggcg gtcgcggacg     360
aggcagaggc ggcggcgctc aaggaggcgg cggcggcgga aaggacgtg cggaggtggc     420 ggcgggtgtg gacgaggcgg cgacgctcgt gggcgcccgg cggagctcgc gaaggtggtg     480
gatggcgcgg tgacgccgtc gctcgtccca gtgggacga tttgtccgc cagtttttgg     540 cggatcggtt ggtcccggat ctga                                            564

<210> SEQ ID NO 12
<211> LENGTH: 187
<212> TYPE: PRT
<213> ORGANISM: Oryza sativa

<400> SEQUENCE: 12

Met Ala Val Ala Val Leu Val Glu Val Ala Ala Val Met Asp Glu Ala
1               5                   10                  15

Glu Glu Ala Pro Gly Ala Glu Arg Arg Arg Leu Asp Leu Ser Gly
            20                  25                  30

Ala Ala Ala Val Leu Ala Glu Val Ala Val Ala Asp Glu Arg Arg His
        35                  40                  45

Ser Trp Arg Arg Arg Arg Pro Trp Arg Arg Gly Gly Ala Arg Gly
    50                  55                  60

Arg Ala Glu Val Ala Ala Val Leu Ala Glu Val Val Ala Asp Glu
65                  70                  75                  80

Arg Arg Ser Ser Trp Arg Arg Leu Arg Arg Pro Arg Arg Gly Gly
                85                  90                  95

Ala Arg Gly Arg Ala Glu Val Val Val Ala Gly Lys Arg Arg Ser
            100                 105                 110

Trp Arg Arg Arg Ser Arg Thr Arg Gln Arg Arg Arg Ser Arg
        115                 120                 125

Arg Arg Arg Arg Arg Arg Thr Cys Gly Gly Gly Gly Cys Gly
    130                 135                 140

Arg Gly Gly Asp Ala Arg Gly Arg Pro Ala Glu Leu Ala Lys Val Val
145                 150                 155                 160

Asp Gly Ala Val Thr Pro Ser Leu Val Pro Gly Gly Thr Ser Leu Ser
                165                 170                 175

Ala Ser Phe Trp Arg Ile Gly Trp Ser Arg Ile
            180                 185

<210> SEQ ID NO 13
<211> LENGTH: 2443
<212> TYPE: DNA
<213> ORGANISM: Oryza sativa

<400> SEQUENCE: 13
ggtaagcgaa gtgtggggaa gtctccttcc cgtccagcca tgcggccata caacctggcc      60 ctcccccac atctcggacg acgcagaggc gcccgggggg cctcggggtg ccacgtcacg     120
ctcctcgggc cctcgggcta cctcgcccca tgcccacgc ccgaccgcca cgtggcggga     180
```

```
ggagtgagtg gggcggtggt cgaagctgaa ccgccatcaa tgcgcagcac cccaaccgtc    240
cctcaccgca tttaatgtgg tgagggcgga cgtgcggcgc tgcccgattg acctgcgtca    300
atcgggcatg accggattgt gaccggtctg tggccggtca cgtccgatcg gataggcggc    360
ggtgccccca cgttccgccc tgtgttcggc ggagttgggg caagtatgcc ccgtcccatc    420
aatgcatcat ctggagctcc ctccacgtga gctgaaccgc caaaagtctc cattcattta    480
aaggggaatg acaagggcgt gtccctgtgt caggcggga acggcgctg ggccccactc      540
gaggacggac ggctgcttag cttccgggcg aaggcacgaa tggtggtccg atccaagcgg    600
catgggtccc cctcccgtga aggagtaggt agaggcggcg catgtggtat ccccttgaac    660
taaaaaagga ggaccttacc caccgaaaag ggacgactct cgattagcct aagccccagg    720
ggaagaagag ttagagttct ccctggagtt gaggaacctt tgtaacactc aaccctaaat    780
cttacacaca ggagtagggt attacgctcc gtagcggccc gaacctgtat aattccagct    840
ctcacgcgca gtctcggaag actctaggcg gatatacgct ctcgatcagc gcgccctttc    900
ccccggccga actcacaaaa gggggggtc actcgatcac ccgctagaga ggatcactcc     960
tcgacagtta tggataccac atacctaata gtagttgact aaatctcggc aggacccacc   1020
acatattatg tcttatacgg aaacaacctt cggatatagg agaagttccg catagggaag   1080
gatgactaga gttctacatg gaaacgacaa ggactacacg gaacaataga tcaagacaca   1140
aaatcaacat acaagccaac atacgccaag acaagacgcc gaatatcgac ttcagagatg   1200
ggcatggcta gtccoctacg gataccgtca ggagagatat agcgctgtct ctgatctcgc   1260
cggatgcgga ttcgaggagg aaggctatcc ttttgtcgac tacgagtcag acctttagac   1320
cactatgtcg acaacagtta gatagactaa cacaaatatt gtactggtgt gattatgatg   1380
aataagcaga cgaccggct tcggccaaca ggatgtaggg ctattccctg acaattcagg    1440
ggcccgaacc tgtataaaaa tcctcgtctc catctctttt actacaatct cgcatatatt   1500
ctaataccaa cgatccccat actatgcaaa aaccggaatc gcgatatcaa acgtcgacag   1560
tattaactaa gagattatat gaaactcact atttgtacat tctcttatat tgctatattt   1620
tagaacaaag aaaatgtttt tgtttttttt tagactgccg ttttccaac tccttttcagc    1680
acctgcccac cgttggattt tcacattttt gctgactgcg gctgcagttc aagtgtgcaa   1740
cccgtgttag gtccggcgcg gtaagtgctg ctggtgtatt tccatttttc ttttcaagta   1800
tatatgtccc cactttgttt tacgaatgca gcacagtagt tttgtagagt aacttttttt   1860
ccctttttagt gatgggaagg cttcgttttg taatacaggt atatatattc agtgattttg   1920
gtcaggggca ccacgtaacg tgagtaagac gctcagtcgc tcacagttta aggaacaaaa   1980
caaaagagga tttactcgca agttaccggg tctggcaatg tgattaaaat cgtagtggtt   2040
acgttcttct tcttcttctt cttcttcttc ttcttctcat atagccatat agggtattac   2100
aagaattcat atggtaggta gtgtaccaat atgacttgga ctatatgtac attttttgct   2160
tctctttttc ttgatttcta gaaaaatgta tcttacagag aaacggcatc ggtcggcagg   2220
ggaaaaaaag gaagaagaag aagaagaaga agaagaagaa gaagaagaag aagaagaaga   2280
agaagaagaa aggagagagg aacagtaacc cgctacatta tcggatagac gaacctgaaa   2340
caaaccagcc atgcatagct ggtaataaag caagttggag gggagaaaga acagtaaaat   2400
gcaggacgtg tcacacggag aaggcagtag gagggcggtg aag                     2443

<210> SEQ ID NO 14
<211> LENGTH: 540
```

```
<212> TYPE: DNA
<213> ORGANISM: Oryza sativa

<400> SEQUENCE: 14
atgcggccat acaacctggc cctcccccca catctcggac gacgcagagg cgcccggggg    60
gcctcggggt gccacgtcac gctcctcggg ccctcgggct acctcgcccc atggcccacg   120
cccgaccgcc acgtggcggg aggaactgcc gttttccaa ctcctttcag cacctgccca   180
ccgttggatt ttcacatttt tgctgactgc ggctgcagtt caagtgtgca acccgtgtta   240
ggtccggcgc gtgatgggaa ggcttcgttt tgtaatacag aaaaatgtat cttacagaga   300
aacggcatcg gtcggcaggg gaaaaaaagg aagaagaaga agaagaagaa gaagaagaag   360
aagaagaaga agaagaagaa gaagaagaaa ggagagagga acagtaaccc gctacattat   420
cggatagacg aacctgaaac aaaccagcca tgcatagctg gtaataaagc aagttggagg   480
ggagaaagaa cagtaaaatg caggacgtgt cacacggaga aggcagtagg agggcggtga   540

<210> SEQ ID NO 15
<211> LENGTH: 179
<212> TYPE: PRT
<213> ORGANISM: Oryza sativa

<400> SEQUENCE: 15

Met Arg Pro Tyr Asn Leu Ala Leu Pro Pro His Leu Gly Arg Arg
1               5                   10                  15

Gly Ala Arg Gly Ala Ser Gly Cys His Val Thr Leu Leu Gly Pro Ser
            20                  25                  30

Gly Tyr Leu Ala Pro Trp Pro Thr Pro Asp Arg His Val Ala Gly Gly
        35                  40                  45

Thr Ala Val Phe Pro Thr Pro Phe Ser Thr Cys Pro Pro Leu Asp Phe
    50                  55                  60

His Ile Phe Ala Asp Cys Gly Cys Ser Ser Val Gln Pro Val Leu
65                  70                  75                  80

Gly Pro Ala Arg Asp Gly Lys Ala Ser Phe Cys Asn Thr Glu Lys Cys
                85                  90                  95

Ile Leu Gln Arg Asn Gly Ile Gly Arg Gln Gly Lys Lys Arg Lys Lys
            100                 105                 110

Lys Lys Lys Lys Lys Lys Lys Lys Lys Lys Lys Lys Lys Lys
        115                 120                 125

Lys Lys Gly Glu Arg Asn Ser Asn Pro Leu His Tyr Arg Ile Asp Glu
    130                 135                 140

Pro Glu Thr Asn Gln Pro Cys Ile Ala Gly Asn Lys Ala Ser Trp Arg
145                 150                 155                 160

Gly Glu Arg Thr Val Lys Cys Arg Thr Cys His Thr Glu Lys Ala Val
                165                 170                 175

Gly Gly Arg

<210> SEQ ID NO 16
<211> LENGTH: 27
<212> TYPE: DNA
<213> ORGANISM: Artificial Sequence
<220> FEATURE:
<223> OTHER INFORMATION: Forward primer for cloning cDNA of OsHDA14 gene

<400> SEQUENCE: 16
gagagataga tccctggagg tttgcag                                         27
```

```
<210> SEQ ID NO 17
<211> LENGTH: 29
<212> TYPE: DNA
<213> ORGANISM: Artificial Sequence
<220> FEATURE:
<223> OTHER INFORMATION: Reverse primer for cloning cDNA of OsHDA14 gene

<400> SEQUENCE: 17
ctggaaagtg caaaagctaa caagacatg                                    29

<210> SEQ ID NO 18
<211> LENGTH: 23
<212> TYPE: DNA
<213> ORGANISM: Artificial Sequence
<220> FEATURE:
<223> OTHER INFORMATION: Forward primer for cloning gDNA of OsZCW7 gene

<400> SEQUENCE: 18
catgggtgtg agtatggggc aag                                          23

<210> SEQ ID NO 19
<211> LENGTH: 23
<212> TYPE: DNA
<213> ORGANISM: Artificial Sequence
<220> FEATURE:
<223> OTHER INFORMATION: Reverse primer for cloning gDNA of OsZCW7 gene

<400> SEQUENCE: 19
gtttggccta gcagctttcg atg                                          23

<210> SEQ ID NO 20
<211> LENGTH: 26
<212> TYPE: DNA
<213> ORGANISM: Artificial Sequence
<220> FEATURE:
<223> OTHER INFORMATION: Forward primer for cloning gDNA of OsCCS1 gene

<400> SEQUENCE: 20
cccatccttc tctctctcca cctaag                                       26

<210> SEQ ID NO 21
<211> LENGTH: 32
<212> TYPE: DNA
<213> ORGANISM: Artificial Sequence
<220> FEATURE:
<223> OTHER INFORMATION: Reverse primer for cloning gDNA of OsCCS1 gene

<400> SEQUENCE: 21
gagttgttgc cacctggtcc atattacagt tc                                32

<210> SEQ ID NO 22
<211> LENGTH: 21
<212> TYPE: DNA
<213> ORGANISM: Artificial Sequence
<220> FEATURE:
<223> OTHER INFORMATION: Forward primer for cloning gDNA of OsDN-DTP10
      gene

<400> SEQUENCE: 22
gaggtggcgg agtttgtgga g                                            21

<210> SEQ ID NO 23
<211> LENGTH: 22
<212> TYPE: DNA
<213> ORGANISM: Artificial Sequence
<220> FEATURE:
<223> OTHER INFORMATION: Reverse primer for cloning gDNA of OsDN-DTP10
```

```
          gene

<400> SEQUENCE: 23
cggtttaggg gtggatggga tg                                          22

<210> SEQ ID NO 24
<211> LENGTH: 34
<212> TYPE: DNA
<213> ORGANISM: Artificial Sequence
<220> FEATURE:
<223> OTHER INFORMATION: Forward primer for cloning gDNA of OsDN-DTP11
      gene

<400> SEQUENCE: 24
ctgctgaggg gtaagcgaag tgtggggaag tctc                             34

<210> SEQ ID NO 25
<211> LENGTH: 33
<212> TYPE: DNA
<213> ORGANISM: Artificial Sequence
<220> FEATURE:
<223> OTHER INFORMATION: Reverse primer for cloning gDNA of OsDN-DTP11
      gene

<400> SEQUENCE: 25
ccgctgaggc ttcaccgccc tcctactgcc ttc                              33

<210> SEQ ID NO 26
<211> LENGTH: 19
<212> TYPE: DNA
<213> ORGANISM: Artificial Sequence
<220> FEATURE:
<223> OTHER INFORMATION: Forward primer for real-time RT-PCR analysis of
      OsHDA14 gene

<400> SEQUENCE: 26
ctacaacctg gagtcgctg                                              19

<210> SEQ ID NO 27
<211> LENGTH: 18
<212> TYPE: DNA
<213> ORGANISM: Artificial Sequence
<220> FEATURE:
<223> OTHER INFORMATION: Reverse primer for real-time RT-PCR analysis of
      OsHDA14 gene

<400> SEQUENCE: 27
tgcttggcct tgtcgatg                                               18

<210> SEQ ID NO 28
<211> LENGTH: 22
<212> TYPE: DNA
<213> ORGANISM: Artificial Sequence
<220> FEATURE:
<223> OTHER INFORMATION: Forward primer for real-time RT-PCR analysis of
      OsZCW7 gene

<400> SEQUENCE: 28
tgtgaggaag atagcgaaaa gg                                          22

<210> SEQ ID NO 29
<211> LENGTH: 21
<212> TYPE: DNA
<213> ORGANISM: Artificial Sequence
<220> FEATURE:
<223> OTHER INFORMATION: Reverse primer for real-time RT-PCR analysis of
      OsZCW7 gene
```

```
<400> SEQUENCE: 29
gatatcctcg tctccgcaaa c                                              21

<210> SEQ ID NO 30
<211> LENGTH: 23
<212> TYPE: DNA
<213> ORGANISM: Artificial Sequence
<220> FEATURE:
<223> OTHER INFORMATION: Forward primer for real-time RT-PCR analysis of
      OsCCS1 gene

<400> SEQUENCE: 30
tgaagataag gagaacatgc cag                                            23

<210> SEQ ID NO 31
<211> LENGTH: 20
<212> TYPE: DNA
<213> ORGANISM: Artificial Sequence
<220> FEATURE:
<223> OTHER INFORMATION: Reverse primer for real-time RT-PCR analysis of
      OsCCS1 gene

<400> SEQUENCE: 31
tcgctgattg aacctctgtg                                                20

<210> SEQ ID NO 32
<211> LENGTH: 18
<212> TYPE: DNA
<213> ORGANISM: Artificial Sequence
<220> FEATURE:
<223> OTHER INFORMATION: Forward primer for real-time RT-PCR analysis of
      OsDN-DTP10 gene

<400> SEQUENCE: 32
gagctcgcga aggtggtg                                                  18

<210> SEQ ID NO 33
<211> LENGTH: 18
<212> TYPE: DNA
<213> ORGANISM: Artificial Sequence
<220> FEATURE:
<223> OTHER INFORMATION: Reverse primer for real-time RT-PCR analysis of
      OsDN-DTP10 gene

<400> SEQUENCE: 33
caaactcgtc ccacctgg                                                  18

<210> SEQ ID NO 34
<211> LENGTH: 22
<212> TYPE: DNA
<213> ORGANISM: Artificial Sequence
<220> FEATURE:
<223> OTHER INFORMATION: Forward primer for real-time RT-PCR analysis of
      OsDN-DTP11 gene

<400> SEQUENCE: 34
acagtaaccc gctacattat cg                                             22
```

```
<210> SEQ ID NO 35
<211> LENGTH: 21
<212> TYPE: DNA
<213> ORGANISM: Artificial Sequence
<220> FEATURE:
<223> OTHER INFORMATION: Reverse primer for real-time RT-PCR analysis of
      OsDN-DTP11 gene

<400> SEQUENCE: 35
gacacgtcct gcattttact g                                              21
```